US010247713B2

(12) United States Patent
Smyth et al.

(10) Patent No.: US 10,247,713 B2
(45) Date of Patent: *Apr. 2, 2019

(54) TIME PASSAGE INDICATOR

(71) Applicant: INSIGNIA TECHNOLOGIES LTD, Newhouse (GB)

(72) Inventors: Erik Smyth, Dundee (GB); Graham Skinner, Glasgow (GB); Deborah Allan, Glasgow (GB)

(73) Assignee: Insignia Technologies LTD, Newhouse (GB)

( * ) Notice: Subject to any disclaimer, the term of this patent is extended or adjusted under 35 U.S.C. 154(b) by 339 days.

This patent is subject to a terminal disclaimer.

(21) Appl. No.: 14/771,180

(22) PCT Filed: Feb. 27, 2014

(86) PCT No.: PCT/GB2014/050585
§ 371 (c)(1),
(2) Date: Aug. 27, 2015

(87) PCT Pub. No.: WO2014/132065
PCT Pub. Date: Sep. 4, 2014

(65) Prior Publication Data
US 2016/0011157 A1    Jan. 14, 2016

(30) Foreign Application Priority Data
Feb. 27, 2013 (GB) .................................. 1303518.3

(51) Int. Cl.
*G01N 21/78* (2006.01)
*G01N 31/22* (2006.01)

(52) U.S. Cl.
CPC ........... *G01N 31/229* (2013.01); *G01N 21/78* (2013.01)

(58) Field of Classification Search
CPC ............................. G01N 31/229; G01N 21/78
See application file for complete search history.

(56) References Cited

U.S. PATENT DOCUMENTS 4,154,107 A * 5/1979 Giezen .................. G01K 11/16
116/207
4,212,153 A * 7/1980 Kydonieus ............... G04F 1/00
116/207

(Continued)

FOREIGN PATENT DOCUMENTS

| WO | 2006077413 A2 | 7/2006 |
| WO | 2010146361 A1 | 12/2010 |
| WO | 2012080704 A1 | 6/2012 |

OTHER PUBLICATIONS

International Search Report from related PCT Application No. PCT/GB2014/050585.

(Continued)

*Primary Examiner* — Lore R Jarrett
(74) *Attorney, Agent, or Firm* — Benesch, Freidlander, Coplan & Aronoff LLP

(57) ABSTRACT

There is described an indicator device for indicating the passage of time, the indicator device comprising an indicator section and a barrier section adjacent thereto, said indicator section comprising: an indicator material; a substrate material; and a first adhesive layer; the indicator material and the substrate material being in the form of one or more layers; the indicator material displaying different visible properties in response to the presence or absence of a chemical agent and/or the concentration thereof; the barrier section comprising a removable barrier layer, the removable barrier layer being substantially impermeable to the chemical agent; wherein on removal of the removable barrier layer, the concentration of the chemical agent in the indicator section changes over time, effecting a visible change. The device (Continued)

may be used to detect the presence/absence of oxygen, water, carbon dioxide, an amine, ammonia, and/or carboxylic acids or to indicate the passage of time.

21 Claims, 8 Drawing Sheets

(56) References Cited

U.S. PATENT DOCUMENTS

| | | | | |
|---|---|---|---|---|
| 4,472,353 | A * | 9/1984 | Moore | G01N 31/224 |
| | | | | 422/401 |
| 5,630,372 | A * | 5/1997 | Ramsey | C12Q 1/26 |
| | | | | 116/206 |
| 5,756,356 | A * | 5/1998 | Yanagi | G01N 31/229 |
| | | | | 116/206 |
| 6,676,901 | B1 * | 1/2004 | Hatakeyama | G01N 31/225 |
| | | | | 422/416 |
| 2006/0110835 | A1 | 5/2006 | Gohil | |
| 2010/0112680 | A1 * | 5/2010 | Brockwell | A61B 5/07 |
| | | | | 435/287.9 |

OTHER PUBLICATIONS

Written Opinion from related PCT Application No. PCT/GB2014/050585.

* cited by examiner

TIME PASSAGE INDICATOR

CROSS-REFERENCE TO RELATED APPLICATIONS

This application is a National stage entry under 35 U.S.C. § 371 of PCT Patent Application No. PCT/GB2014/050585, filed Feb. 27, 2014, which claims priority to United Kingdom Patent Application No. GB 1303518.3, filed on Feb. 27, 2013, each of which is hereby incorporated by reference.

FIELD OF INVENTION

The present invention relates to an indicator device a method for preparing an indicator device, and products derived therefrom. In particular, the present invention relates to a laminated indicator device comprising an oxygen and/or water sensitive, carbon dioxide sensitive, acid/carboxylic acid sensitive or an ammonia sensitive ink which can be activated using, for example, UV light, a reducing agent or carbon dioxide. The products derived therefrom may include, for example, a multilayer adhesive tape or sticker, which can be used to detect oxidising agents, oxygen, water, reducing agents, UV light, carbon dioxide, ammonia, temperature and the passage of time. A further example of the use of the indicator device is as a time-temperature history indicator.

Perishable goods, and in particular drinks and foodstuffs, are often provided in some form of air-tight packaging. This packing can be applied in a modified atmosphere (known as modified atmosphere packaging (MAP)), which limits the presence of oxygen and which often involves purging the packaging with carbon dioxide. Alternatively, perishable goods may be packaged in normal atmospheric conditions.

Items that are packaged in air-tight packaging include: food, beverages, works of art, pharmaceuticals, medical diagnostic kits and sterilised packages. As mentioned, it is particularly desirable in the food industry to package goods such that their exposure to oxygen after packaging is minimised. This can be used to effectively extend the shelf life of many perishable items.

BACKGROUND ART

It is useful to be able to determine the length of time for which a package containing perishable goods has been opened. To this end, many different sensors for detecting oxidising agents, and in particular for detecting oxygen, have been produced. Several of these sensors have been adapted for attachment to packages containing perishable goods. For example, GB 2419868, FR 2836677, WO 2006/077413, GB 2344101 and US 2006/0110835 disclose the use of oxygen sensitive dyes that are covered by a seal, the seal being broken by the opening of a package, and the dye changing colour over a set period of time to indicate the duration for which the package has been opened.

WO 03/021252 (incorporated herein by reference) discloses a sensor for oxidising agents which is activated using UV light. This patent application discusses the use of a particular chemical composition which can be in the form of an ink, and which may be printed onto a variety of supports. However, the indicator disclosed is necessarily sensitive to oxygen. It is not apparent from reading the application how such an indicator may be effectively integrated with, or printed onto, packaging in the reduced form. In addition, it is unclear as to how such an indicator may be applied in the reduced form in atmospheric conditions. Also, there is no indication regarding how such an indicator might be incorporated into a multi-layered product.

The composition described in WO 03/021252 comprises at least one redox-sensitive material, at least one semiconductor material and at least one electron donor. The intimate contact of the various components of the indicator allows the redox sensitive material to undergo a redox reaction wherein there is a transfer of electrons from the photogenerated reduced form of the semiconductor material to the redox sensitive material.

The redox-sensitive material can be a dye such as a thiazine dyestuff, an oxazine dyestuff, an azine dyestuff, a triphenylmethane dyestuff, an indophenol dyestuff, an indigo dyestuff, viologen and/or mixtures thereof.

The semiconductor material has the ability to form an excited electronic state that is sufficiently oxidising to oxidize the sacrificial electron donor and has a reduced form that is able to reduce the redox sensitive material.

The semiconductor material may be an oxide of titanium (such as titanium (IV) oxide; $TiO_2$, and strontium titanate; $SrTiO_3$), tin (such as tin (IV) oxide; $SnO_2$), tungsten (such as tungsten (VI) oxide; $WO_3$) and zinc (such as zinc (II) oxide; ZnO) and mixtures thereof.

The electron donor has the ability to donate electrons, preferably irreversibly. Typically, the electron donor is a mild reducing agent. The electron donor may, for example, be an amine (e. g. NaEDTA and TEOA), reducing saccharide (such as glucose and fructose), readily oxidisable polymer (such as polyvinyl alcohol), and other general anti-oxidant (such as ascorbic and citric acid) or easily oxidizable material (such as glycerin) and/or mixtures thereof.

The indicator may further comprise a binder which binds all the components together. The binder may be a polymeric material such as gelatin, hydroxyethyl cellulose (HEC), polyvinyl alcohol (PVA), ethyl cellulose (EC), cellulose acetate (CEA), polypyrolidone (PVP), polyethylene oxide, and polymethylmethacrylate (PMMA).

Many modern day printing processes, and many types of modern packaging, require the use of organic solvent based inks. This is also the case in the preparation of a multi-layered indicator device. Whilst it is stated in WO 03/021252 that the indicator compositions can be combined with an organic solvent to provide an ink or printable solution, the inventors have found that the redox active species tends to leach out of such solutions.

Generally a composition comprising the indicator compositions of WO 03/021252 will be unstable upon addition to, for example, food packaging. Typically, such a composition will break down upon addition to food packaging as the dye contained therein, upon contact with water contained in the food packaging or the atmosphere, will tend to leach out of the composition. Furthermore, the redox active species can leach out of solution following storage under ambient conditions, meaning that a solution of the composition is not suitable for use in printing.

The inks and indicator compositions described in WO 03/021252 are therefore not suitable for use in many modern day printing processes, which require the use of organic solvent based inks, or in the application to many types of modern packaging, which require that the compositions are stable (i.e., resistant to leaching) on exposure to water.

Furthermore, it can be impractical to activate indicator compositions (incorporated into inks) after they have been printed and sealed on a substrate, such as packaging. For example, it can be difficult to expose the printed indicator composition to the correct amount of UV light in a controlled fashion, particularly as most printing processes do not have the time window to allow such exposure. Also, exposing the indicator composition to UV light after printing and sealing requires additional specialised equipment to be used in the printing process, and makes the process more complicated and time-consuming. Known UV activatable inks are unsuitable for activation before printing as they will change colour (i.e., oxidise) before or during the printing process.

In addition, in the catering industry, it is not uncommon for foods to be prepared and then used in the subsequent days. It is critical for food safety that the caterers keep a note of when the food was prepared. Sometimes this is done using a colour coding system, or it can simply be done by the caterer keeping a written or a mental note of when the food was prepared. Sometimes, different caterers use different coding systems which can lead to confusion and, ultimately, the provision of unfit foods to the customer, or the disposal of edible foods. Similarly, the keeping of written or mental notes often results in the loss of information, and thus can potentially lead to the provision of unfit foods to the customer, or the disposal of edible foods.

A similar situation occurs in the home environment, particularly in connection with products that must be used within a certain number of days of opening. For example, it is not uncommon for products such as fresh fruit juice or pre-packaged meats, and even long shelf life items such as pickles and conserves, to have to be used within a number of days, weeks or months from opening. It is almost impossible for the consumer to keep track of the date on which each of these items was opened. Again, this can potentially lead to the consumption of unfit foods, or to the disposal of edible foods.

Therefore, it is an object of the present invention to obviate or mitigate at least some of the disadvantages of the prior art.

A further object of the invention is to provide an indicator device that can be applied to foodstuffs, or food or drink packaging.

Further objects of the invention are to provide a method for preparing an indicator device, and a method of detecting atmospheric conditions (such as oxygen, water, UV light, carbon dioxide or ammonia) using an indicator device.

DISCLOSURE OF INVENTION

According to a first aspect of the invention there is provided an indicator device for indicating the passage of time, the indicator device comprising an indicator section and a barrier section adjacent thereto, the indicator section comprising:
   an indicator material;
   a substrate material; and
   a first adhesive layer;
the indicator material and the substrate material being in the form of one or more layers; the indicator material displaying different visible properties in response to the presence or absence of a chemical agent and/or the concentration thereof;
   the barrier section comprising a removable barrier layer, the removable barrier layer being substantially impermeable to the chemical agent;
   wherein on removal of the removable barrier layer, the concentration of the chemical agent in the indicator section changes over time, effecting a change in visible properties of the indicator material.
The indicator device is a laminate, or multi-layered, product.

The indicator material may be part of a composition. Depending in the nature of the indicator material, the indicator material, or indicator composition, may be activated by UV light, a reducing agent, an oxidising agent, carbon dioxide, a base, an alkali or an acid.

The indicator device may be used to detect a change in atmospheric conditions. The atmospheric conditions being detected may be the presence or absence of an oxidising agent, oxygen and/or water, carbon dioxide or ammonia. Alternatively the indicator device may be configured to detect UV light, a reducing agent. Furthermore, the indicator device may be configured to detect a change (increase or decrease) in the amount (i.e., the concentration) of any of these components in the atmosphere, or a change in pH. The "atmosphere" may be a confined space such as, for example, the atmosphere surrounding a (optionally hermetically) sealed foodstuff of beverage.

The indicator section may comprise the chemical agent, wherein on removal of the removable barrier layer, the concentration of the chemical agent in the indicator section decreases over time.

The chemical agent may diffuse out of the indicator section.

The barrier section may also provide a semi-permeable seal configured to allow controlled flow to the indicator of the chemical agent that effects a change in visible properties of the indicator material.

The indicator device may further comprise a second adhesive layer, optionally as part of the indicator section.

The indicator material may be incorporated into a discrete indicator layer and the substrate material may incorporated into a discrete substrate layer, separate to the indicator layer.

The first adhesive layer and the indicator layer may be adjacent the substrate layer.

The substrate layer may be located between the first adhesive layer and the indicator layer.

The first adhesive layer may be adjacent a first side of the substrate layer, and the indicator layer may be adjacent a second side of the substrate layer.

The substrate layer may have a thickness of between approximately 50 µm and 100 µm.

The substrate layer may be selected from one or more of the group consisting of: aluminium oxide foil, polypropylene, and polyethylene terephthalate; and platinised versions thereof.

The indicator layer may have a thickness of between approximately 1 µm and 3 µm.

The barrier section may be adjacent the indicator layer.

The second adhesive layer may be adjacent the indicator layer.

The indicator layer may further comprise a reference section, optionally comprising a reference ink.

The reference section may be adjacent the second adhesive layer.

The indicator layer may be divided into two or more portions, a first portion comprising the reference section and a second portion comprising the indicator material.

The indicator layer may be divided into two or more portions, wherein the first portion comprises the indicator material after exposure to the chemical agent, and the second portion comprises the indicator material before exposure to the chemical agent or vice versa, at least one of the first and second portions acting as a reference section.

The barrier section may be sized to cover only one of the first and second portions.

The first adhesive layer may be larger in width than the indicator layer in at least one axis such that the adhesive layer caps the indicator layer by covering a first side of the indicator layer and by covering one or more edges of the indicator layer.

The barrier section may be larger in width than the indicator layer in at least one axis.

The first adhesive layer may be larger in width than the substrate layer in at least one axis such that the adhesive layer caps the substrate layer by covering a first side of the substrate layer and by covering one or more edges of the substrate layer.

The barrier section may be larger in width than the substrate layer in at least one axis.

The indicator layer may further comprise an organic solvent soluble polymer; typically an organic solvent soluble polymer comprising hydrophobic backbone and a plurality of electronically charged sidechains; most typically at least partially-sulfonated polystyrene.

Typically the at least partially-sulfonated polystyrene is from about 10% to about 30% sulphonated.

In one embodiment the indicator layer further comprises an electron donor. Typically the electron donor is an amine, a reducing saccharide, a readily oxidisable polymer, a polyol, glycerol, trihydroxyhexane and/or a general antioxidant.

The indicator layer may further comprise at least one semiconductor material specifically sensitive to light having a wavelength of about 200-400 nm. Typically the semiconductor material is an oxide of: titanium, tin, tungsten, zirconium, zinc or mixtures thereof.

In an alternative embodiment the indicator layer further comprises a reducing agent and/or the oxidation products therefrom. Typically the reducing agent is selected from one or more of the group consisting of: dithionites, sulphites, and ascorbic acid; and/or acceptable salts thereof; and/or the oxidation products therefrom.

The reducing agent may include further components. For example, when the reducing agent is ascorbic acid, it may also comprise hydrochloric acid.

The indicator layer may comprise a polymer binder optionally selected from one or more of the group consisting of: polyvinyl butyral (PVB), nitrocellulose (NC), polyvinyl alcohol (PVA), hydroxyethyl cellulose (HEC), and hydroxypropyl cellulose (HPC).

The indicator layer may comprise a plasticiser optionally selected from one or more of the group consisting of: tributyl phosphate, diisodecyl adipate, tris-2-ethylhexyl phosphate, tributyl phosphate, glycerol and dimethyl phthalate.

The indicator material and the substrate material may be incorporated into the same layer so-forming a combined indicator and substrate layer, wherein the indicator material is dispersed within the substrate material or vice versa.

That is to say that the indicator material and the substrate material are in a single layer, and there is no need for separate indicator and substrate layers. In this embodiment, the combined indicator and substrate layer acts as both an indicator layer and a substrate layer.

The combined indicator and substrate layer may comprise a polymer composite, said polymer composite comprising at least one thermoplastic polymer, and at least one chemical indicator dispersed in the at least one thermoplastic polymer, the at least one chemical indicator comprising a particulate inorganic substrate, and at least one reactive dye or ink coated on and/or impregnated within the particulate inorganic substrate.

A particulate inorganic substrate is understood to be defined as a substrate which is typically made of an insoluble material, and which is provided in a particulate form. This typically includes inorganic fillers and/or inorganic pigments, which may be white, transparent, or coloured. In the context of the invention an insoluble material is understood to be defined as a material that is insoluble in a water-based or organic solvent in which the indicator material or composition ink is intended to be dissolved, prior to coating and/or impregnating within the particulate inorganic substrate.

The particulate inorganic substrate may be in powder form. Typically, the particulate inorganic substrate may be an inorganic pigment, e.g. silica, titania, alumina, magnesium oxide, calcium oxide or a zeolite.

The at least one chemical indicator may be substantially uniformly dispersed in the at least one polymer.

The polymer composite may comprise a melt-processed polymer composite, preferably extruded, and may be provided in the form of e.g. a film, sheet, tube, or any other suitable profile.

The at least one thermoplastic polymer may comprise an addition polymer such as a polyolefin, e.g. polyethylene or polypropylene, or another thermoplastic addition polymer, e.g. polystyrene or a polyacrylate. Alternatively, the at least one thermoplastic polymer may comprise a condensation polymer, e.g. polycarbonate, polyether, polyester, polyamide or polyacetal.

In one embodiment, the at least one thermoplastic polymer may be a hydrophobic polymer, e.g. polyethylene. In such instance, the at least one chemical indicator may comprise a hydrophobic particulate inorganic substrate, e.g. hydrophobic silica or hydrophobic alumina.

The combined indicator and substrate layer may have a thickness of between approximately 50 to 70 μm.

The combined indicator and substrate layer may be adjacent the first adhesive layer.

The combined indicator and substrate layer may be located between the first adhesive layer and the second adhesive layer.

The barrier section may be adjacent the combined indicator and substrate layer.

The second adhesive layer may be adjacent the combined indicator and substrate layer.

The combined indicator and substrate layer may further comprise a reference section, optionally comprising a reference ink.

The reference section may be adjacent the second adhesive layer.

The combined indicator and substrate layer may be divided into two or more portions, a first portion comprising the reference section and a second portion comprising the indicator material.

The combined indicator and substrate layer may be divided into two or more portions, wherein the first portion comprises the indicator material after exposure to the chemical agent, and the second portion comprises the indicator material before exposure to the chemical agent or vice versa, at least one of the first and second portions acting as a reference section.

The barrier section may be sized to cover only one of the first and second portions.

The first adhesive layer may be larger in width than the combined indicator and substrate layer in at least one axis such that the adhesive layer caps the combined indicator and substrate layer by covering a first side of the combined indicator and substrate layer and by covering one or more edges of the combined indicator and substrate layer.

The barrier section may be larger in width than the combined indicator and substrate layer in at least one axis.

The indicator material may be selected from one or more of the group consisting of: a redox sensitive material, a carbon monoxide sensitive material, a carbon dioxide sensitive material, an oxygen sensitive material, an amine sensitive material and an ammonia sensitive material.

The redox sensitive material may be selected from one or more of the group consisting of: a thiazine dyestuff, an oxazine dyestuff, an azine dyestuff, a triphenylmethane dyestuff, an indophenol dyestuff, an indigo dyestuff, a redox sensitive metal complex, proflavin and viologen.

The carbon dioxide sensitive material may be selected from one or more of the group consisting of: m-Cresol Purple (MCP, Hydroxy triarylmethane), Thymolphthalein (3,3-bis(4-hydroxy-2-methyl-5-propan-2-ylphenyl)-2-benzofuran-1-one), o-Cresolphthalein, Acryloly florescein (AcF1), 13-methyl umbelliferon (BMUB), Bromothymol blue (BTB, Hydroxy triarylmethane), 5' and 6-Carboxyseminaphtholfluorescein (c-SNAFL), S' and 6'-Carboxyseminaphtholrhodamine (c-SNARF), Cresol Red (CR, o-Cresolsulfonephthalein), Hexadecyl trimethyl ammonium cation (CTA), Hexadecyl trimethyl ammonium hydroxide (CTAH), Dual lumophore referencing (DLR), 2-(2,4-Dinitrophenylaxo)-1-naphthol-3,6-disulphonic acid (DNPA), tris(thenoyltrifluoroacetonato) europium (III) (Eu(tta)1), Fluorescein (FI, resorcinolphthalein), 7-hydroxycoumarin-4-acetic acid (HCA), 1, Hydroxypyrene-3,6,S-trisulphonic acid (HPTS), Neutral red (NR, toluylene red), Phenol Red (PR, phenolsulfonphthalein), Rhodamine 6G (R6G), Sulforhodamine 101 (SRh), Thymol blue (TB, thymolsulphonephthalein) and Texas Red hydrazine (THR).

It will be appreciated that that any other suitable pH-sensitive dye or ink can be used.

The amine or ammonia sensitive material may be selected from one or more of the group consisting of: Bromophenol Blue (BPB, Hydroxy triarylmethane), Bromocresol Green (BCG, Hydroxy triarylmethane), Bromocresol Purple (BCP, Hydroxy triarylmethane), Bromothymol Blue (BTB, Hydroxy triarylmethane), Phloxine Blue (PB, Fluorone), Thymol Blue (TB, Hydroxy triarylmethane), and m-Cresol Purple (MCP, Hydroxy triarylmethane).

The first adhesive layer or second adhesive layer may have a thickness of between approximately 1 μm and 3 μm.

The first adhesive layer or second adhesive layer may be selected from one or more of the group consisting of: a rubber based hot melt, an acrylic adhesive, a varnish coated adhesive, an adhesive kill treated adhesive, a treated or coated permanent acrylic, and a treated or coated peelable acrylic.

The indicator device may further comprise a release section adjacent the indicator section and detachable therefrom.

The release section may be adjacent the first adhesive layer and is detachable therefrom.

The release section may comprise a release layer, said release layer adjacent the first adhesive layer and detachable therefrom.

The release layer may have a thickness of between approximately 50 μm and 100 μm, typically between 60 μm and 70 μm.

The release layer may be selected from one or more of the group consisting of: glassine, siliconised glassine paper, and a silicon treated polymer.

The indicator section may be located between the release section and the barrier section.

The barrier section may further comprise a coating layer.

The barrier section may comprise a barrier layer and the second adhesive layer, said second adhesive layer being adjacent the indicator section.

Typically, at least one of the second adhesive layer and the coating layer are adjacent the barrier layer.

The barrier layer may be located between the second adhesive layer and the coating layer.

The second adhesive layer may be adjacent a first side of the barrier layer, and the coating layer is adjacent a second side of the barrier layer.

The coating layer may provide a semi-permeable seal.

The barrier layer may have a thickness of between approximately 12 μm and 300 μm, typically between 30 μm and 200 μm.

The barrier layer may be selected from one or more of the group consisting of: polyethylene, polyethylene terephthalate, ethylene vinyl alcohol, polyvinylidene chloride, polyvinyl alcohol, low density polyethylene, polypropylene, polyester and aluminium oxide coated polyethylene terephthalate.

The barrier section may comprise a reference ink.

The barrier section may comprise a detachable section and a fixed section.

The detachable section and the fixed section may be attached by a frangible area.

The barrier section may further comprise a tab.

The coating layer may have a thickness of between approximately 1 μm and 3 μm.

The coating layer may be selected from one or more of the group consisting of: polyethylene terephthalate, ethylene vinyl alcohol, polyvinylidene chloride, polyvinyl alcohol, and aluminium oxide coated polyethylene terephthalate.

The indicator section may further comprise a silicone polymer or additive. The chemical agent may be at least one of an oxidising agent, water, carbon dioxide, amines, acids, carboxylic acids, ammonium hydroxide and ammonia.

The chemical agent may be selected from one or more of the group consisting of: ammonia, ammonium hydroxide, propylamine, butylamine, hexylamine, octylamine, ethanoic acid, propanoic acid, and butanoic acid.

The indicator section may further comprise a phase transfer agent.

The phase transfer agent may be located in the indicator layer or the combined indicator and substrate layer. The phase transfer agent may be a quaternary ammonium cation or base.

The indicator section may further comprises a chemical species which deprotonates the indicator material.

The chemical species which deprotonates the indicator material may be located in the indicator layer or the combined indicator and substrate layer.

The chemical species which deprotonates the indicator material may be a quaternary ammonium cation or base.

According to a second aspect of the invention, there is provided a package comprising the indicator device as described in first aspect.

According to a third aspect of the invention, there is provided a method of detecting the passage of time, comprising the steps of:
 a) providing an indicator device as described in the first aspect; and
 b) subsequently detecting a visible change in the indicator material whereby the passage of time is revealed.

The method may comprise the further step of removing a barrier layer from an indicator layer or a combined indicator and substrate layer to allow the concentration of a chemical agent in the indicator section to change over time, thereby effecting a change in visible properties of the indicator material.

The indicator device of the present invention can be applied to foodstuffs and the like by end users in the home. Alternatively, it can be used in a commercial setting such as the catering and retail industries. The indicator device enables accurate assessment of the amount of time since a foodstuff was first exposed to air or opened, or the amount of time since a foodstuff was prepared. Therefore, the indicator device can be used to indicate when a foodstuff is no longer fit for consumption. This helps to prevent both consumption of unfit foodstuffs and the unnecessary disposal of consumable foodstuffs.

Embodiments of the invention will now be described, by way of example only, with reference to the drawings, in which.

MODES FOR CARRYING OUT THE INVENTION

Redox Active Indicators

Figure 1:
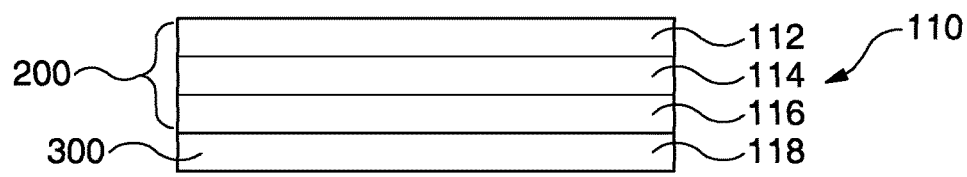
FIG. 1 is a cross section of a laminated tape.

Most colourimetric oxygen indicators rely on a reaction between a redox-sensitive indicator dye, such as methylene blue, and a strong reducing agent, such as glucose in a strongly alkaline (pH>12) environment. This reaction leads to the reduction of the redox-sensitive dye and concomitant colour change. The redox dye is readily reoxidised back to its original colour upon exposure to oxygen. Known indictors comprising a redox-sensitive dye, a sacrificial electron donor and a semiconductor photoactive material have been described for the detection of oxygen in WO 03/021252. However, such dyes are not usable in most organic solvents, as the redox-sensitive dye used tends to leach out of solution.

Although the following discussion is limited to that of oxygen it should be realised that the discussion is applicable to any other type of oxidising agents.

The novel oxygen indicator described utilises at least one redox-sensitive dye (eg. a thiazine dyestuff, oxazine dyestuff, azine dyestuff, triphenylmethane dyestuff, indophenol dyestuff, indigo dyestuff, viologen or a mixture thereof). The redox-sensitive dye is chosen so that, at the levels employed in the oxygen indicator, it has little or no absorbance in the near UV, i.e. 300-400 nm. The redox-sensitive dyestuff is also chosen so that its reduced form has a different colour, and/or fluorescence, to its oxidised form and is oxidised to the latter by oxygen.

The oxygen indicator utilises a sacrificial electron donor (SED), which is a mild reducing agent, such as a polyol, in particular gycol, or triethanolamine (TEOA), or the disodium salt of ethylenediammine tetraacetic acid (NaEDTA). The mild reducing agent is selected on the basis that, at the levels employed in the oxygen indicator, it: (a) does not reduce the redox-sensitive dye at a significant rate under either aerobic or anaerobic conditions and (b) does not reductively quench the electronically excited state of the redox-sensitive dye under either aerobic or anaerobic conditions. These conditions being satisfied, the combination of redox-sensitive dye and mild reducing agent is stable and long-lived under ambient atmospheric and typical room-light conditions. Note that no strong alkaline material is present in the oxygen indicator since the latter turns many mild reducing agents, such as reducing sugars, TEOA and NaEDTA into strong reducing agents, and conditions (a) and (b) would no longer be satisfied.

A near UV-absorbing semiconductor photoactive material (SC) is also present in the oxygen indicator. The role of the semiconductor is to initiate the process of indicator activation by absorbing some of the burst of near UV light that the indicator is exposed to. Absorption of a photon of near UV light by the semiconductor material in particle, film (micro or nanocrystalline) or single crystal form leads to the creation of a photogenerated electron-hole pair.

The semiconductor material is selected so that the photogenerated electron is sufficiently reducing in power that it can reduce the redox-sensitive dye present and the hole is sufficiently oxidising that it can oxidise the mild reducing agent present. The net effect upon UV activation of the combination of semiconductor material/redox-sensitive dye/ sacrificial electron donor that goes to make the oxygen indicator is that the dye is converted to its differently coloured, or fluorescent, reduced, oxygen-sensitive, form. For example, methylene blue (which is blue) is reduced to leuco-methylene blue (which is colourless) and the sacrificial electron donor, or mild reducing agent, is oxidised, i.e. SED to SEDox; both latter species are usually colourless.

The overall scheme can be represented by the following series of reaction equations:

Light Activation Step (Under Anaerobic Conditions)

$$SC + h\nu \rightarrow SC(e^-; h^+)$$

Where hv represents the energy of an absorbed photon; the latter will have an energy greater than or equal to the bandgap energy of the semiconductor (SC), i.e. an ultra-bandgap photon. For the present invention the most favoured semiconductors will have large bandgaps (3-4 eV) and so will require excitation by near UV light. SC ($e^-$; $h^+$) represents an electronically excited form of the semiconductor, SC, and will have a photogenerated electron, SC ($e^-$), and a photogenerated hole, SC ($h^+$) available for reaction.

Scavenging of the Photogenerated Electron $$SC(e^-; h^+) + Ox \rightarrow Red + SC(h^+)$$

Where Ox is the aerobically (and anaerobically) stable, coloured form of the redox sensitive dye and Red is the reduced form of Ox which not only is markedly different in colour, and/or fluorescence, to Ox but also reacts readily with oxygen and, consequently, is only stable under anaerobic conditions.

Scavenging of the Photogenerated Hole $$SC(h^+) + SED \rightarrow SC + SED^+$$

The mild reducing agent, SED, is chosen so that it does not react directly with Ox, as is the case for most other colourimetric oxygen indicators, and so that it preferably reacts irreversibly with the photogenerated hole.

Oxygen Indicating Step $$Red + O_2 \rightarrow Ox + H_2O$$

The reduced form of the redox sensitive dye is stable under anaerobic conditions. However, upon exposure to oxygen the reaction noted above takes place and the original colour (i.e. that seen before light activation) and/or fluorescence of the indicator returns, thus indicating the presence of oxygen.

In one embodiment of the present invention the indicator also comprises an organic solvent soluble polymer which can bind the redox-sensitive material by ionic bonding, at least when the redox-sensitive material is in the oxidised form. The polymer can have a hydrophobic backbone and electronically charged sidechains. For example, the polymer can be partially-sulfonated polystyrene or another suitable polymer that has at least some electronically charged, or sufficiently polar, sidegroups that have sufficient affinity for the redox dye to mitigate leaching of the dye under storage or on exposure to organic solvents or water, to produce an ink that is useable in the printing process.

The oxygen indicator can be re-used simply by reactivating with ultra-bandgap light, the preferred wavelength range of which falls in the near UV. Note that the oxygen indicator is not selective towards oxygen, but will also respond to most strong oxidising agents if they are present, such as chlorine, nitrogen dioxide and ozone.

This lack of selectivity towards oxygen is also a feature of almost all other oxygen indicators. Fortunately, in most packages (especially food) and the ambient environment, there are no, or very little, oxidising agents other than oxygen. The sensitivity of the oxygen indicator towards oxidising gases other than oxygen may be exploited to create indicators for these other gases.

The oxygen sensing action of the oxygen indicator is irreversible in that it only works after it has been activated by exposure to near UV light. Once oxidised, it cannot be reactivated unless it is deliberately exposed again to near UV light.

Typical ambient room light does not possess sufficient UV light to drive this light activation process at a significant rate. Although prolonged exposure to sunlight can drive the light activation step forward, most packaged goods, including food, also suffer unwanted deleterious effects if exposed to bright sunlight. As a consequence, under the typical lighting conditions employed in handling most packaged goods, the oxygen indicator will not be activated.

The dyestuff brings about the colour change exhibited. The dyestuffs that can be used include: thiazine dyestuffs (such as methylene blue, thionin and toluidine blue), oxazine dyestuffs (such as resazurin, safranine O, and celestine blue), azine dyestuffs, (such as cresyl violet acetate and azure A), indophenol dyestuffs (such as dichloroindophenol), indigo dyestuffs (such as indigo and indigo carmine), viologens (such as heptyl and benzyl viologen) and mixtures thereof.

The organic solvent soluble polymer binds with the dyestuff to ensure that the dyestuff remains soluble in organic solvent. Organic solvent soluble polymers that can be used include partially-sulfonated polystyrene or another suitable hydrophobic, anionic, organic solvent soluble polymer.

The semiconductor material drives the reduction of the redox-sensitive dye by the sacrificial electron donor, upon absorption of some of the near UV light used to activate, i.e. make sensitive towards oxygen, the oxygen indicator. The semiconductor material may be used in various forms, including: as micro and nanocrystalline powder particles dispersed in a polymer encapsulating material or pressed in the form of a tablet or pellet, or as a micro or nanocrystalline film. The semiconductor material is usually biologically and chemically inactive, unless irradiated with light of energy greater than or equal to its bandgap. Ideally, the bandgap of the semiconductor should fall in the near UV region, i.e. 3.1 to 4.1 eV (400 to 300 nm). Typically the semiconductor should be selected from a group that includes the oxides of titanium (such as titanium (IV) oxide; $TiO_2$, and strontium titanate; $SrTiO_3$), tin (such as tin (IV) oxide; $SnO_2$), tungsten (such as tungsten (VI) oxide; $WO_3$) and zinc (such as zinc (II) oxide; ZnO) and mixtures thereof. The sacrificial electron acceptor is any species that reacts readily with the photogenerated hole on the semiconductor but does not react directly or significantly with either the redox-sensitive dye (under aerobic or anaerobic conditions) or with oxygen (under aerobic conditions).

Examples of such a sacrificial electron donor can be found amongst the following categories: amines (such as NaEDTA and TEOA), reducing saccharides (such as glucose and fructose), readily oxidisable polymers, and other general anti-oxidants (such as ascorbic and citric acid), polyols (such as glycerol), trihydroxyhexane and mixtures thereof. Although some of the above are sometimes cited as examples of strong reducing agents (such as glucose and TEOA), this is only the case if a strong alkali is also present. In the present invention no strong alkali is used and all sacrificial electron donors cited above are as a consequence only mildly reducing.

As an alternative, the sacrificial electron donor and the semiconductor material may be replaced by a reducing agent. Suitable reducing agents include: dithionites, such as sodium dithionite; sulphites, such as sodium sulphite borohydrides, such as sodium borohydride; and ascorbic acid.

The reducing agent may include further components. For example, when the reducing agent is ascorbic acid, it may also comprise hydrochloric acid. In contrast to the sacrificial electron donors discussed above, the reducing agents in this context must have sufficient strength to reduce the indicator compound (for example, methylene blue) from the oxidised to the reduced state. The sacrificial electron donors cannot do this without the additional input of the semiconductor material and UV light.

A particularly good reducing agent is dithionite, such as sodium dithionite.

When combined with a suitable solvent, the initial form of the oxygen indicator is as an ink or castable solution that can be printed or cast on a wide variety of supports. Examples of typical solvents that can be used include: ketones (such as acetone), alkylhalides (such as chloromethane), esters (such as ethyl acetate) and aromatics (such as toluene).

Examples of Preparation of Ink for Indicator Layer

Solvent based inks were prepared as described below. One type of ink comprises partially sulfonated-polystyrene (a polymer binder), glycerol (a sacrificial electron donor), nanorutile titanium dioxide (a photocatalyst) and methylene blue (a dye). A second type of ink comprises partially sulfonated-polystyrene (a polymer binder), sodium dithionite (a reducing agent) and methylene blue (a dye).

Preparation of Sulfonated Polystyrene

The sulfonated polystyrene (SPS) used was prepared in-house by the direct sulfonation of polystyrene as described in previous literature (C. R. Martins et al, Journal of the Brazilian Chemical Society, 14 (2003) No. 5; Makowski et al, U.S. Pat. No. 3,870,841 (1975); R. A. Weiss et al, Journal of Polymer Science: Polymer Chemistry Edition, 23 (1985) pp 525-533).

Initially, 52 g of polystyrene (average molecular weight 250,000, supplied by Acros Organics) was placed in a 3-necked, round-bottomed flask and to it was added 245 mL of dichloromethane (DCM). The solution was stirred vigorously on a magnetic stirrer to promote dissolution of the polymer, typically requiring 1 to 2 hours for complete dissolution.

Whilst the polystyrene was dissolving, acetyl sulphate (which acts as the sulfonating agent) was prepared. 49 mL of DCM was placed in a conical flask sealed with a rubber septum stopper, and to it was carefully added 9.5 mL of acetic anhydride via a syringe. The resulting solution was immediately placed under an argon atmosphere and cooled using an ice bath. Once sufficiently cool, and once the polystyrene had dissolved in the DCM, 3.5 mL of 95% sulphuric acid was added dropwise to the DCM/acetic anhydride mixture, thus converting the acetic anhydride to acetyl sulphate. Once all of the sulphuric acid had been added, the acetyl sulphate was removed from the argon atmosphere. 35 mL of acetyl sulphate was then extracted and subsequently added to the stirred polystyrene solution.

After addition of the acetyl sulphate, two of the three necks of the round-bottomed flask were sealed with rubber septum stoppers, and the flask was transferred to an oil bath on a hotplate stirrer. A reflux condenser was attached to the free neck of the round-bottomed flask, and the hotplate was set to a constant 40° C. using a fuzzy logic temperature control attachment. Once at 40° C., the stirring solution was left under reflux for 4 hours. During this time the solution typically changes colour from colourless to a pale blue. Also note that, whilst not strictly necessary, the degree of sulfonation of the polystyrene tends to increase if the refluxing solution is bubbled gently with argon over the 4 hour period. By increasing the degree of sulfonation, the SPS is found to be more soluble in both acetone and ethyl acetate. The degree of sulfonation is approximately 10%.

After 4 hours, the solution was removed from reflux (and from the argon atmosphere if applicable) and to it was added 50 mL of ethanol. Upon addition, a white precipitate was visible. The solution was gently swirled to aid the distribution of the ethanol throughout the round-bottomed flask before the mixture was poured slowly and carefully into 1.75 L of boiling water. As it was added, the sulfonated polystyrene precipitated rapidly, hence it was necessary to stir the boiling water, preferably through the use of both a magnetic stirrer and a glass/plastic rod operated manually. It was also necessary to add the sulfonated polystyrene solution in stages, removing the precipitate at regular intervals to increase yield. Once complete, the precipitate was washed with water several times before being transferred to a vacuum desiccator for drying. For best results, the precipitate was left overnight to dry. Typically the synthesis, as outlined above, yields ca. 50 g of SPS.

A batch of enhanced polarity sulfonated polystyrene was prepared for use in making indicator compositions that could be used to prepare ethanol based inks. The method used was identical to that described above, except the amount of acetyl sulphonate used in the sulfonation step was increased to 105 mL (i.e., 3 times as much acetyl sulfonate was used). The resulting enhanced polarity sulfonated polystyrene was soluble in ethanol, but insoluble in both ethyl acetate and water. The degree of sulfonation is approximately 30%.

Preparation of Solvent-Based Ink

A solvent based UV activatable oxygen sensitive ink was prepared as follows.

350 mg of SPS was weighed into a small sample vial and to it was added 2 g of acetone. The solution was gently stirred until all the polymer had dissolved. To the solution was then added 250 mg of glycerol (the sacrificial electron donor, SED), and the solution was again gently stirred to improve dissolution thereof.

100 mg of nanorutile titanium dioxide (the photocatalyst) was then added. The solution was then stirred until all of the photocatalyst had dispersed. Once the photocatalyst had fully dispersed, 2.5 mg of methylene blue (the redox active dye) was added, and the resulting solution was sealed in the sample vial using Parafilm (Trade Mark) to mitigate evaporation of acetone. The ink was then stirred, usually overnight, to ensure that all of the methylene blue had dissolved, to provide a solvent based UV activatable, oxygen sensitive ink. Note that 2.5 to 5 mg of methylene blue can be used depending on the desired intensity of "blue" colour. For ethanol based inks, around 30 to 40 mg of methylene blue can be used. This is shown in the ethanol ink example below.

An alternative solvent that can be used in place of acetone is ethyl acetate. It is particularly desirable to use ethyl acetate as most ink manufacturers regard it as a suitable solvent for printing inks. An ethyl acetate based ink was also prepared.

The acetone based ink was found to have a viscosity of 64.7 cP, and the viscosity of the ethyl acetate based ink was found to be 379.6 cP (for reference, water has a viscosity of 0.894 cP and glycerol has a viscosity of 1500 cP). These viscosities make these inks suitable for use in many printing processes such as Gravure printing and flexography.

An alternative solvent that can be used is ethanol, to provide an ethanol based ink. An ethanol based UV activatable, oxygen sensitive ink, in accordance with one embodiment of the present invention, was prepared as follows.

40 mg of methylene blue was added to a sample bottle, to which was added 5 g of ethanol and 2 g of deionised water. The bottle was then closed and sonicated for 10 minutes before the solution was left to gently stir until all the methylene blue had mixed well. After all the methylene blue had dissolved, 500 mg of the enhanced polarity SPS was then added to the solution. The solution formed a gel like substance within the sample bottle as soon as the enhanced polarity SPS was added. The sample bottle was sonicated for approximately 40 minutes, then left to stir gently to facilitate the gel reforming into a solution.

400 mg of glycerol was added to the solution, which was then stirred for 10 to 15 minutes. 300 mg of semi-conductor material (nanorutile titania) was then added to the sample bottle. The sample bottle was then sealed with Parafilm™ to prevent evaporation of the solvent, and the solution was sonicated for a further 5 minutes. The solution was then stirred until all the powder had dispersed.

A further ethanol based ink was prepared as follows. 250 mg of enhanced polarity SPS was weighed into a small sample vial and to it was added 2 g of ethanol. The solution was gently stirred until all the polymer had dissolved. To the solution was then added 250 mg of glycerol (the sacrificial electron donor, SED), and the solution was again gently stirred to improve dissolution thereof.

100 mg of nanorutile titanium dioxide (the photocatalyst) was then added. The solution was then stirred until all of the photocatalyst had dispersed. Once the photocatalyst had fully dispersed, 30 mg of methylene blue (the redox active dye) was added. The resulting solution was sealed in the sample vial, and the ink was stirred to ensure that all of the methylene blue had dissolved, providing a solvent based UV activatable, oxygen sensitive ink.

A further ethanol based ink was prepared using the techniques described above, further incorporating water. The amounts of materials used in the ink were: 3 g of ethanol; 1 g of water; 500 mg of enhanced polarity SPS; 250 mg of trihydroxyhexane; 100 mg of nanorutile titania; and 30 mg of methylene blue.

A solvent based non-UV activatable oxygen sensitive ink was prepared largely as outlined above with the exception that sodium dithionite (a reducing agent) was added in place of the semiconductor material and the sacrificial electron donor material. The ink consisted of 200 mg of partially sulphonated polystyrene, 2 g of ethanol, 800 mg water and 16 mg methylene blue. To this mixture is added 0.5 ml of 0.43M sodium dithionite (approximately 37 mg). On addition of sodium dithionite a colour change from blue to light yellow is observed indicating reduction of the methylene blue. Thus the ink may comprise sodium dithionite and/or the product of the oxidation of the sodium dithionite such as thiosulfate and bisulphite.

Other solvent based non-UV activatable inks were prepared using different ratios of ethanol to water such as: 2 g ethanol and 500 mg water, giving a solvent mix which is 80% by weight ethanol and 20% by weight water.

In the preparation of this type of ink, the partially sulphonated polystyrene, the solvent and the indicator material are combined as described in the foregoing paragraphs. The reducing agent is then added to this mixture to provide a colour change from blue to colourless/light yellow as the methylene blue is reduced from the oxidised to the reduced form.

The organic solvent used can be one or a mixture of various alcohols such as methanol and ethanol, acetone or ethyl acetate, and may be combined with water.

Activation of the Inks

The inks were activated before experimental studies were carried out. To activate the UV activatable ink, UVA light is required. In brief, irradiation of $TiO_2$ with electromagnetic radiation (i.e. light) of a wavelength less than ca. 380 nm results in the formation of a hole-electron pair. The hole, which is positively charged, reacts with the SED (glycerol) and oxidises it, whilst the negatively charged electron can be used for dye reduction. Reduction of the dye alters its electronic structure, thus causing a colour change to occur.

A 2×8 W, UVA lamp, fitted with Black Light Blue (BLB) bulbs was used to activate the samples. The peak wavelength of UVA light emitted by such bulbs occurs at ca. 365 nm. By placing the lamp flush with the sample under test, a UVA output of ca. 3 mW cm$^{-2}$ is achieved. Ordinarily, around two minutes of UVA irradiation is required to initiate a colour change from blue to colourless for acetone derived compositions. However, by using a higher intensity UVA source, activation of the ink could be achieved more rapidly.

Surprisingly, it has been found that ethyl acetate derived compositions bleach more quickly than acetone derived compositions, typically changing colour after only one minute of exposure to UVA irradiation. Thus ethyl acetate based inks, and the dry compositions therefrom, can be activated twice as quickly as acetone based inks and compositions.

The non-UV activatable inks were activated by the addition of sodium dithionite (or an alternative suitable reducing agent) as described above.

Other inks that can be used with the device of the present invention can be prepared by combining a binder material (often a polymer), a dye and a plasticiser. A solvent is typically added to make a printable ink solution. Also, an amine may be added to activate the dye. Typical formulations are as illustrated below.

Example Ink Formulation 1

50 g of 15% w/v polyvinyl butyral and 5 ml of 40 mg/ml bromophenol blue in ethanol were combined to make a first solution. 4 g of this first solution were combined with 0.1 ml of 28-30% ammonium hydroxide and 0.2 ml of tributyl phosphate to create an ink.

The resulting ink when printed and stored in the refrigerator changes colour with 1 to 2 weeks.

Example Ink Formulation 2

50 g of 15% w/v polyvinyl butyral and 5 ml of 20 mg/ml Bromophenol blue in ethanol were combined to make a first solution. 4 g of this first solution were combined with 30 μl of hexylamine and 0.3 ml of tributyl phosphate to create an ink.

The resulting ink when printed and stored in the refrigerator changes colour over 3 months.

Example Ink Formulation 3

50 g of hydraCOAT HV 1105 S F and 5 ml of 160 mg/ml bromophenol blue in ethanol were combined to make a first solution. 4 g of this first solution were combined with 0.1 ml of 28-30% ammonium hydroxide and 0.1 ml of tributyl phosphate to create an ink.

The resulting ink when printed and stored in the refrigerator changes colour over 3 weeks.

Example Ink Formulation 4

Solution I:
1.6 g Phenol Red in 10 ml Ethanol
8 ml 1M NaOH (aq.)
Ink:
10 g of 15% w/w Hydroxypropyl cellulose (HPC) in ethanol
4 ml of Solution I
2 ml ethanol
0.08 g glycerol Acidified Ink:
   1.5 g of Ink+0.5 ml 5% v/v ethanoic acid (aq.)

All solutions were prepared by adding the components in the order they appear and left to stir for at least 30 minutes before subsequently using. The "Acidified Ink" is printed down on a white backing and immediately coated with a layer of 15% w/w polyvinyl butyral (PVB) in ethanol. Immediately after printing, the ink is yellow, but over time changes to orange, red and finally pink.

The rate at which the colour change takes place (typically minutes to days) can be controlled by:
   Varying the glycerol concentration;
   Varying the amount of ethanoic acid; and/or
   Varying the thickness of the PVB overcoat.

It should be noted that using dyes with different pKas will also vary the rate of colour change.

In order to stop the colour change, a barrier film can be adhered on top of the ink.

Typically the ink comprises of a binder (polymer), a pH-sensitive dye, plasticiser, a volatile amine and a suitable solvent. After the ink is printed, the volatile amine will slowly evaporate, decreasing the pH, which subsequently results in a colour change of the pH-sensitive dye. The time at which this colour change occurs can be varied by altering the ink formulation.

Amines

Using volatile amines with higher boiling points results in indicators which change colour over longer periods of time and using volatile amines with low boiling points results in indicators with relatively quick colour changes.

Amines that can be used include: ammonia, ammonium hydroxide, propylamine, butylamine, hexylamine and octylamine.

Acids

Using volatile acids with higher boiling points results in indicators which change colour over longer periods of time and using volatile acids with low boiling points results in indicators with relatively quick colour changes.

Acids that can be used include carboxylic acids such as, for example: ethanoic acid, propanoic acid, butanoic acid, and other higher carbon chain carboxylic acids.

Plasticiser

Higher quantities of plasticiser typically shortens the time the indicators take to change colour, whereas decreasing the plasticiser content lengthens the time.

Plasticisers that can be used include diisodecyl adipate, tris-2-ethylhexyl phosphate, tributyl phosphate and dimethyl phthalate. Without wishing to be bound by theory, it is thought that in one embodiment glycerol acts as a plasticiser.

Binder

Different polymers have different permeabilities to volatile amines, hence changing the polymer can alter the times. Since the timers are based on diffusion, the timers take longer to change colour at lower temperatures than higher temperatures (i.e. a timer stored in the fridge will take longer to change colour than when stored at room temperature).

Polymer binders that can be used include polyvinyl butyral (PVB), nitrocellulose (NC), polyvinyl alcohol (PVA), hydroxyethyl cellulose (HEC) and hydroxypropyl cellulose (HPC).

In order to stop the ink from changing colour, a suitable barrier film (typically polyethylene terephthalate, PET) is applied onto the label, which can be removed when the pack is opened.

Preparation of Combined Indicator and Substrate Layer

The combined indicator and substrate layers were prepared in accordance with the procedure and materials outlined in GB 2474571, the contents of which are incorporated herein by reference.

Silica (silicon dioxide) and alumina (aluminium oxide) were chosen as inorganic substrates for preparation of the indicators. Silica pigment was found to be a particularly suitable inorganic substrate because of its wide utilisation as a polymer filler, low cost, ready availability, ease of handling, safety, and lack of colour (white). Indicators were prepared using both hydrophobic pigments (silica or alumina), and hydrophilic pigments (silica or alumina).

Titania was also used in connection with the preparation of oxygen-sensitive indicators. Titania was chosen because it is a semiconducting material which can act as a photocatalyst in the reduction and thus the activation of certain oxygen-sensitive dyes.

A variety of reactive dyes were employed to make the indicators. The choice of dye in each case was based upon the substance to be detected. The dyes that were used in the preparation of carbon dioxide-sensitive indicators were: m-cresol purple, phenolphthalein, phenol red, cresol red, o-cresolphthalein, thymolphthalein, thymol blue and naphthol blue black.

The dyes that were used in the preparation of ammonia-sensitive indicators were: bromophenol blue, bromocresol green, bromocreso, purple, bromothymol blue, phloxine blue, thymol blue and m-cresol purple.

The dyes that were used in the preparation of oxygen-sensitive indicators were: methylene blue, thionine, azure B, Nile blue, ruthenium tris bipyridyl, tris(4,7-diphenyl-1,10-phenanthrolione) ruthenium (II) perchlorate, platinum (II) octaethyl porphyrin ketone and proflavin.

Hydrophobic Silica or Alumina for $CO_2$ Indicators

Approximately 0.04 g of reactive dye (indicator material) was added to a beaker containing 2.0 g of hydrophobic silica (Degussa/Evonik Aerosil R812; S.S.A.=260+/−30 $m^2$/g; average particle size=7 nm) and approximately 100 mL of methanol. 1 mL of 1M tetrabutylammonium hydroxide in methanol was added. The mixture was well stirred/sonicated, the resulting solution was transferred to a round-bottomed flask and the methanol removed with the aid of a rotary evaporator at 30° C. under vacuum. The resultant powder was removed and ground into a fine powder using a pestle and mortar.

Pigments based on hydrophobic alumina (Degussa/Evonik Aeroxide Alu C805), rather than silica were also prepared as above and proved equally effective.

Alternative bases to tetrabutylammonium hydroxide can also be used, including sodium hydroxide and sodium bicarbonate.

Alternative solvents to methanol can also be used, including ethanol and ethyl acetate.

Hydrophilic Silica or Alumina for $CO_2$ Indicators

Typically, a lower ratio of dye to inorganic pigment was used with hydrophilic silica (Degussa/Evonik Aerosil 300) and hydrophilic alumina (Degussa/Evonik Aeroxide Alu C).

To 15.0 g of hydrophilic silica (Degussa/Evonik Aerosil 300), 0.12 g of reactive dye was added. Approximately 100 mL water and 12 mL of 1.5 M tetrabutylammonium hydroxide in water was added. After stirring, the solvent (water) was evaporated under reduced pressure to produce to produce a fine powder.

Pigments based on hydrophilic alumina (Degussa/Evonik Aeroxide Alu C), rather than silica were also prepared as above and proved equally effective.

Hydrophobic Silica or Alumina for $NH_3$ Indicators

Approximately 1 g of reactive dye (indicator material) was added to a beaker containing 4.0 g of hydrophobic silica (Degussa/Evonik Aerosil R812; S.S.A.=260+/−30 $m^2$/g; average particle size=7 nm) and approximately 80 mL of methanol. The mixture was well stirred/sonicated, the resulting solution was transferred to a round-bottomed flask and the solvent removed with the aid of a rotary evaporator at 30° C. under vacuum. The resultant powder was removed and ground into a fine powder using a pestle and mortar.

Pigments based on hydrophobic alumina (Degussa/Evonik Aeroxide Alu C805), rather than silica were also prepared as above and proved equally effective.

Hydrophilic Silica or Alumina for $NH_3$ Indicators

Typically, a lower ratio of dye to inorganic pigment was used with hydrophilic silica (Degussa/Evonik Aerosil 300) and hydrophilic alumina (Degussa/Evonik Aeroxide Alu C).

Approximately 0.5 g of reactive dye (indicator material) was added to a beaker containing 40 g of hydrophilic silica (Degussa/Evonik Aerosil 300) and approximately 80 mL of water. The mixture was well stirred/sonicated, the resulting solution was transferred to a round-bottomed flask and the solvent (water) removed with the aid of a rotary evaporator at 30° C. under vacuum. The resultant powder was removed and ground into a fine powder using a pestle and mortar.

Pigments based on hydrophilic alumina (Degussa/Evonik Aeroxide Alu C), rather than silica were also prepared as above and proved equally effective.

Hydrophobic Silica or Alumina for Luminescence-Based $O_2$ Indicators

To 2.0 g of hydrophobic silica (Degussa/Evonik Aerosil R812, S.S.A.=260+/−30 $m^2$/g, average particle size=7 nm), 2 mg of an oxygen-sensitive luminescent dye, such as PtOEPK or Rudpp (tetraphenyl borate salt) was added in 100 mL of a suitable solvent (THF for PtOEPK or acetone for Rudpp). The mixture was mixed thoroughly and the solvent was removed under reduced pressure using a rotary evaporator. The resultant powder was removed and ground into a fine powder using a pestle and mortar. Pigments based on hydrophobic alumina (Degussa/Evonik Aeroxide Alu C805), rather than silica were also prepared as above and proved equally effective.

Hydrophilic Silica or Alumina for Luminescence-Based $O_2$ Indicators

To 2.0 g of hydrophilic silica (Degussa/Evonik Aerosil 300), 2 mg of an oxygen-sensitive luminescent dye, such as Rudpp (chloride salt) was added in 100 mL of a polar solvent such as ethanol or water. The mixture was mixed thoroughly and the solvent was removed under reduced pressure using a rotary evaporator. The resultant powder was removed and ground into a fine powder using a pestle and mortar.

Pigments based on hydrophilic alumina (Degussa/Evonik Aeroxide Alu C), rather than silica were also prepared as above and proved equally effective.

Titania

Titania was used in connection with the preparation of certain oxygen-sensitive indicators. Titania was chosen because, in particular grades, it is a semiconducting material which can act as a photocatalyst in the reduction and thus the activation of certain oxygen-sensitive indicators. Because titania must be able to act as more than a support and drive the photoreduction of the dye to a form that is oxygen sensitive, the titania inorganic substrate was chosen in an untreated form so as to preserve its photocatalytic properties.

Solvent-Based Pigment for $O_2$ Indicators

To 2.0 g of titanium dioxide (Degussa/Evonik P25), 10 mg of reactive dye, 1.0 g of DL-Threitol and approximately 100 mL of ethanol were added. The mixture was mixed thoroughly and then the solvent (ethanol) removed under reduced pressure using a rotary evaporator. The resultant powder was removed and ground into a fine powder using a pestle and mortar.

Water-Based Pigment for $O_2$ Indicators

To 2.0 g of titanium dioxide (Degussa/Evonik P25), 10 mg of reactive dye, 1.0 g of DL-Threitol and approximately 100 mL of water were added. The mixture was mixed thoroughly and then the solvent (water) removed under reduced pressure using a rotary evaporator. The resultant powder was removed and ground into a fine powder using a pestle and mortar.

Incorporation in Polymer a) Hydrophobic Polymers

Polyethylene was chosen as a particularly suitable hydrophobic polymer due to its low cost, ease of manufacture and processability, and wide range of applications, including food packaging and medical applications.

In order to be compatible with polyethylene, the indicators used for incorporation into such polymer films were indicators based on hydrophobic silica, hydrophobic alumina, or untreated titania.

Typically 0.4 g of the hydrophobic indicator was added to 2.0-4.0 g of powdered polyethylene. The two powders were further ground until the colour was uniform. A small sample of the resulting powder was heat pressed at 115° C. for 5 minutes under 5 tonnes pressure using a Specac Atlas™ Series Heated Platens, before being allowed to cool. A 0.1 mm-thick plastic film was obtained.

This procedure is similar to that used in making extruded polymer films in which the pigment is dispersed, thus producing very thin polymer films.

b) Hydrophilic Polymers

Polyethylene oxide was chosen as a suitable hydrophilic polymer. In order to be compatible with polyethylene oxide, the indicators used for incorporation into such polymer films were indicators based on hydrophilic silica, hydrophilic alumina, or untreated titania.

Typically 0.4 g of the hydrophilic indicator was added to 2.0-4.0 g of powdered polyethylene oxide. The two powders were further ground until the colour was uniform. A small sample of the resulting powder was heat pressed at 65° C. for 5 minutes under 5 tonnes pressure using a Specac Atlas™ Series Heated Platens, before being allowed to cool. A 0.1 mm-thick plastic film was obtained.

Example Combined Indicator and Substrate Layer

A 10% bromophenol blue in aqueous hydrophilic silica (Aerosil 150) dispersion was prepared. This was then spray-dried to produce a dry free-flowing 'intelligent pigment'.

A masterbatch formulation was prepared according to the following formula:
59.5% by weight low density polyethylene (LDPE)
20.0% by weight linear low density polyethylene (LLDPE)
20% by weight intelligent pigment (from above)
0.5% by weight zinc stearate.

The masterbatch was used to make an indicator film having a combined indicator and substrate.

The prepared indicator film has a three layer co-extruded structure, in which the core layer contains intelligent pigment at 5% by weight. The outer layers generally consist of LDPE or medium density polyethylene (MDPE), however these can be varied to give varying film properties.

The resulting yellow film was then exposed to ammonia vapour which turned the film blue. This film is then used to construct the indicator/substrate layer of an indicator device.

Monitoring of the Indicator Device

The bleaching of indicator devices and their subsequent recovery (oxidation) was recorded photographically. In addition, or alternatively, the recovery of the film compositions was monitored by diffuse reflectance spectroscopy using a hand-held Konica-Minolta CM-2500d Spectrophotometer.

EXAMPLES

Referring now to FIG. 1, there is shown at 110 an indicator device in accordance with one embodiment of the invention. The indicator device 110 has an indicator section 200 placed next to a release section 300. The indicator section 200 consists of an aluminium oxide substrate layer 114 located between an indicator layer 112 (which contains the ink as described above) and a varnish coated acrylic adhesive layer 116. The release section 300 contains a glassine release layer 118 (also known as a release liner).

The indicator section 200 and the release section 300 are arranged so that the adhesive layer 116 is in contact with the release layer 118. The release liner 118 protects the adhesive layer 116 until such time that the indicator device 110 is to be attached to an item.

Figure 2:
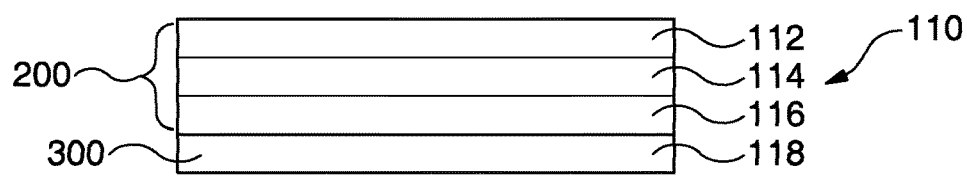
FIG. 2 is a cross section of an alternative laminated tape.

Referring now to FIG. 2, there is provided at 110 an indicator device in accordance with one embodiment of the invention. The indicator device 110 has an indicator section 200 placed next to a release section 300. The indicator section 200 consists of a polypropylene substrate layer 114 located between an indicator layer 112 (which contains the ink as described above) and a varnish coated acrylic adhesive layer 116. The release section 300 contains a glassine release layer 118 (also known as a release liner).

The indicator section 200 and the release section 300 are arranged to that the adhesive layer 116 is in contact with the release layer 118. The release liner 118 protects the adhesive layer 116 until such time that the indicator device 110 is to be attached to an item.

In use, the indicator devices 110 as illustrated in FIGS. 1 and 2 are applied to foodstuffs or packaging either before or after they are sealed and/or opened, depending on anticipated colour change duration of the indicator layer, and the longevity of the product to which it is attached. To apply the indicator devices 110, the indicator section 200 is removed from the release section 300 (which is typically discarded) and the adhesive layer 116 is used to apply the indicator section 200 to the product or packaging allowing the indicator layer 112 to be exposed to atmospheric conditions.

Figure 3:
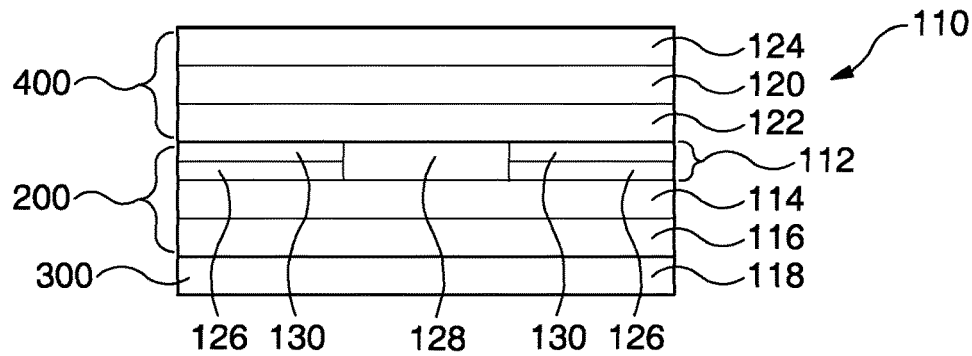
FIG. 3 is a cross section of an one embodiment of the invention in which the laminated tape includes a barrier section.

Referring now to FIG. 3, there is provided at 110 an indicator device in accordance with one embodiment of the invention. The indicator device 110 has an indicator section 200 situated between a release section 300 and a barrier section 400, and in contact therewith. The indicator section 200 consists of a polypropylene substrate layer 114 located between an indicator layer 112 (which contains the ink as described above) and a varnish coated acrylic adhesive layer 116. The barrier section 400 contains a clear polyethylene terephthalate barrier layer 120 located between an ethylene vinyl alcohol coating layer 124 and a varnish coated acrylic adhesive layer 122. The release section 300 contains a glassine release layer 118 (also known as a release liner).

The indicator layer 112 is split into sections, the central section including a redox active ink 128. The outer section(s) are further divided in half horizontally. The lower half includes a silicone polymer 130 printed on the substrate 114, and the upper half includes a reference ink 126, which is printed on top of the silicone polymer layer 130.

The indicator section 200 is located between the release section 300 and the barrier section 400. The indicator section 200 and the release section 300 are arranged so that the adhesive layer 116 is in contact with the release layer 118. The release layer 118 protects the adhesive layer 116 until such time that the indicator device 110 is to be attached to an item. The indicator section 200 and the barrier section 400 are arranged so that the indicator layer 112 is in contact with the adhesive layer 122 of the barrier section 400. The barrier section 400 protects the indicator layer 112 until a time that a user wishes to demarcate.

In use, the barrier section 400 may be removed and the indicator layer 112 exposed when a foodstuff is packaged or opened. Alternatively, the barrier section 400 may be removed and the indicator layer 112 exposed when a prepared foodstuff is put into short term storage, thus illustrating for how long a foodstuff has been stored. This is particularly useful in the catering industry.

Figure 4:
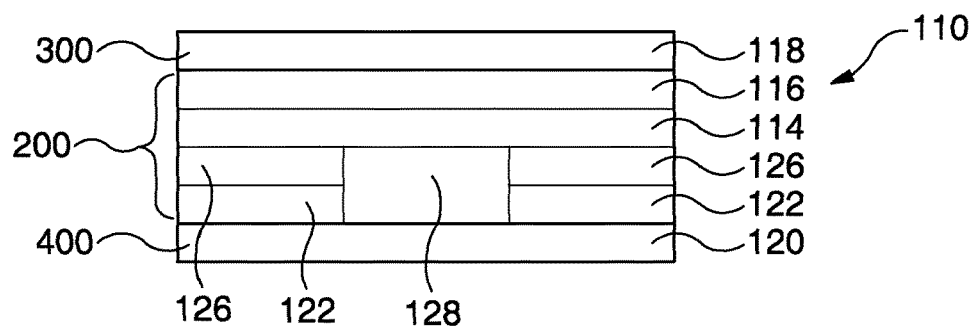
FIG. 4 is a cross section of an alternative embodiment of the invention suitable for application to the inside of packaging.

Referring now to FIG. 4, there is provided at 110 an indicator device in accordance with one embodiment of the invention. The indicator device 110 has an indicator section 200 situated between a release section 300 and a barrier section 400, and in contact therewith. The indicator section 200 consists of a polyethylene terephthalate substrate layer 114 located between an indicator layer 112 (which contains the ink as described above) and a varnish coated acrylic adhesive layer 116. On the other side of the indicator layer 112 there is a patterned adhesive layer 122. The indicator layer 112 is split into sections, the central section including a redox active ink 128, and the outer section(s) including a reference ink 126. The inks 126, 128 are printed onto the substrate 114. The patterned adhesive layer 122 is printed onto the reference ink 126 but does not come into contact with the redox active ink 128. The barrier section 400 contains a low density polyethylene or polyethylene terephthalate barrier layer 120. The release section 300 contains a glassine release layer 118 (also known as a release liner).

The indicator section 200 is located between the release section 300 and the barrier section 400. The indicator section 200 and the release section 300 are arranged so that the adhesive layer 116 is in contact with the release layer 118. The release layer 118 protects the adhesive layer 116 until such time that the indicator device 110 is to be attached to an item. The indicator section 200 and the barrier section 400 are arranged so that the adhesive layer 122 of the indicator section 200 is in contact with the barrier layer 120 of the barrier section 400. In this embodiment the barrier section 400 is not designed to be removed, but slows ingress of atmospheric conditions to the indicator layer 112. For example, the barrier section 400 may slow the ingress of oxygen when applied to the inside of packaging.

Figure 5:
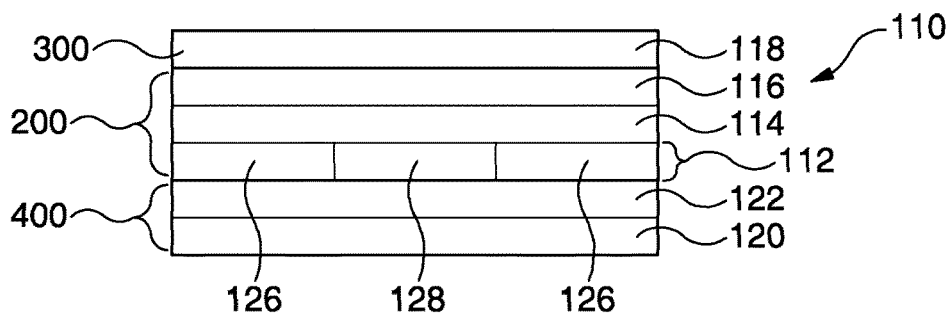
FIG. 5 is a cross section of a further alternative embodiment of the invention also suitable for application to the inside of packaging.

Referring now to FIG. 5, there is provided at 110 an indicator device in accordance with one embodiment of the invention. The indicator device 110 has an indicator section 200 situated between a release section 300 and a barrier section 400, and in contact therewith. The indicator section 200 consists of a polyethylene terephthalate substrate layer 114 located between an indicator layer 112 (which contains the ink as described above) and a varnish coated acrylic adhesive layer 116. The indicator layer 112 is split into sections, the central section including a redox active ink 128, and the outer section(s) including a reference ink 126. The inks 126, 128 are printed onto the substrate 114. The barrier section 400 contains a low density polyethylene or polyethylene terephthalate barrier layer 120, and a patterned adhesive layer 122. The patterned adhesive layer is attached to the reference ink 126 but does not come into contact with the redox active ink 128. The release section 300 contains a glassine release layer 118 (also known as a release liner).

The indicator section 200 is located between the release section 300 and the barrier section 400. The indicator section 200 and the release section 300 are arranged so that the adhesive layer 116 is in contact with the release layer 118. The release layer 118 protects the adhesive layer 116 until such time that the indicator device 110 is to be attached to an item. The indicator section 200 and the barrier section 400 are arranged so that the indicator layer 112 is in contact with the adhesive layer 122 of the barrier section 400. In this embodiment the barrier section 400 is designed to be removed before use.

Figure 6:
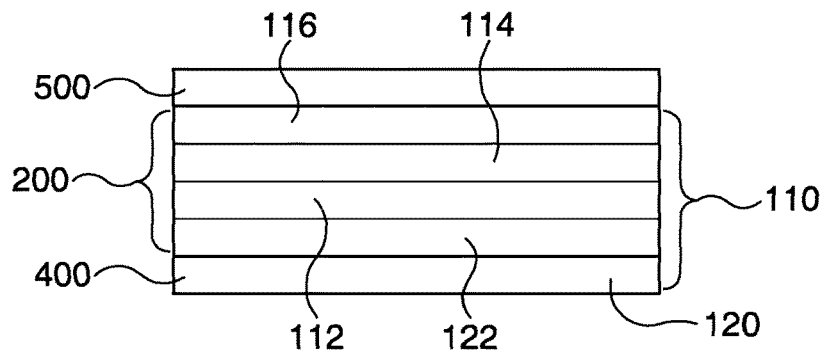
FIG. 6 is a cross section of one embodiment of the invention wherein a laminated sticker is applied to the inside of packaging.

Referring now to FIG. 6, there is provided at 110 an indicator device in accordance with one embodiment of the invention, and attached to packaging material 500. The indicator device 110 has an indicator section 200 situated between the packaging 500 and a barrier section 400, and in contact therewith. The indicator section 200 consists of a polyethylene terephthalate substrate layer 114 located between an indicator layer 112 (which contains an indicator material as described above) and an acrylic adhesive layer 116. The indicator section 200 comprises a further adhesive layer 122, located such that the indicator layer 112 is between the substrate layer 114 and the adhesive layer 122. It will be understood that the adhesive layer 122 could also be located in the barrier section 400. The barrier section 400 contains a low density polyethylene, polyester or polypropylene barrier layer 120.

The indicator device 110 is attached to packaging 500, such that the indicator layer 112 is visible to a user through the packaging 500. Thus, the substrate layer 114 is transparent or translucent. The indicator device 110 is constructed and located in such a way that selected atmospheric species (e.g., carbon dioxide, oxygen, water and ammonia) can reach the indicator layer 112, via the barrier layer 120. The barrier layer 120 may be selected such that it is "food safe". That is to say that it is made from a material approved for use next to foodstuffs. It will be appreciated that the ordering of the indicator layer 112 and the substrate layer 114 can be swapped, provided that the substrate layer 114 is chosen to enable passage of selected atmospheric species (e.g., carbon dioxide, oxygen, water and ammonia) to the indicator layer 112.

Figure 7:
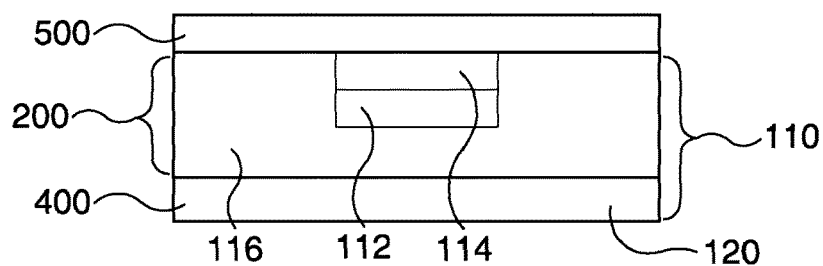
FIG. 7 is a cross section of a laminated sticker applied to the inside of packaging in accordance with an alternative embodiment.

Referring now to FIG. 7, there is provided at 110 an indicator device in accordance with one embodiment of the invention, and attached to packaging material 500. The indicator device 110 has an indicator section 200 situated between the packaging 500 and a barrier section 400, and in contact therewith. The indicator section 200 consists of a polyethylene terephthalate substrate layer 114 located between an indicator layer 112 (which contains an indicator material as described above) and an acrylic adhesive layer 116. The acrylic adhesive layer 116 also covers the sides of the substrate layer 114 and the indicator layer 112. The barrier section 400 contains a low density polyethylene or polyethylene terephthalate barrier layer 120. The barrier section 400 contains a low density polyethylene, polyester or polypropylene barrier layer 120. The substrate layer 114 and the indicator layer 112 are smaller in diameter than the barrier layer 120, the barrier layer 120 in combination with the adhesive layer 116 effectively acting as a "cap", which encapsulates the substrate layer 114 and the indicator layer 112, and affixes them to the packaging 500. It will be understood that the adhesive layer 116 could also be located in the barrier section 400.

The indicator device 110 is attached to packaging 500, such that the indicator layer 112 is visible to a user through the packaging 500. Thus, the substrate layer 114 is transparent or translucent. The indicator device 110 is constructed and located in such a way that selected atmospheric species (e.g., carbon dioxide, oxygen, water and ammonia) can reach the indicator layer 112, via the barrier layer 120. The barrier layer 120 may be selected such that it is "food safe". That is to say that it is made from a material approved for use next to foodstuffs. It will be appreciated that the ordering of the indicator layer 112 and the substrate layer 114 can be swapped, provided that the substrate layer 114 is chosen to enable passage of selected atmospheric species (e.g., carbon dioxide, oxygen, water and ammonia) to the indicator layer 112.

Figure 8:
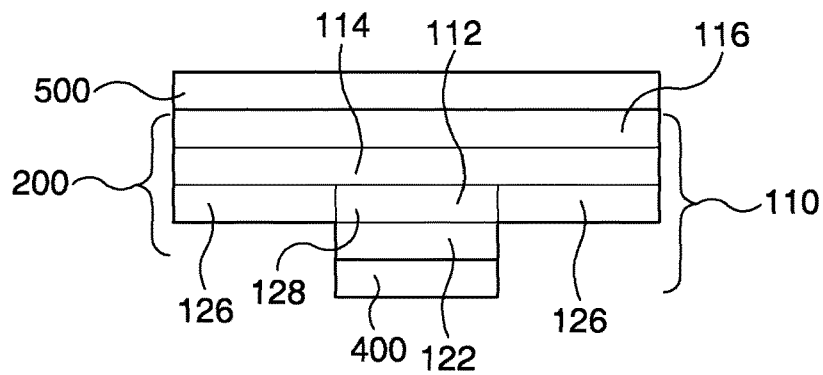
FIG. 8 is a cross section of a laminated sticker applied to the inside of packaging in accordance with a further alternative embodiment.

Referring now to FIG. 8, there is provided at 110 an indicator device in accordance with one embodiment of the invention, and attached to packaging material 500. The indicator device 110 has an indicator section 200 situated between the packaging 500 and a barrier section 400, and in contact therewith. The indicator section 200 consists of a polyethylene terephthalate substrate layer 114 located between an indicator layer 112 (which contains an indicator material as described above) and an acrylic adhesive layer 116. The indicator section 200 comprises a further adhesive layer 122, located such that the indicator layer 112 is between the substrate layer 114 and the adhesive layer 122. It will be understood that the adhesive layer 122 could also be located in the barrier section 400. The indicator layer 112 is split into sections, the central section 128 including an indicator material, and the outer section(s) 126 including a reference material. The inks used are printed onto the substrate 114. The barrier section 400 contains a low density polyethylene, polyester or polypropylene barrier layer 120. The barrier section 400 and barrier layer 120 cover only the central section 128 including an indicator material, and not the outer section(s) 126 including a reference material.

The indicator device 110 is attached to packaging 500, such that the indicator layer 112 is visible to a user through the packaging 500. Thus, the substrate layer 114 is transparent or translucent. The indicator device 110 is constructed and located in such a way that selected atmospheric species (e.g., carbon dioxide, oxygen, water and ammonia) can reach the indicator layer 112, via the barrier layer 120. The barrier layer 120 may be selected such that it is "food safe". That is to say that it is made from a material approved for use next to foodstuffs. It will be appreciated that the ordering of the indicator layer 112 and the substrate layer 114 can be swapped, and provided that the substrate layer 114 is chosen to enable passage of selected atmospheric species (e.g., carbon dioxide, oxygen, water and ammonia) to the indicator layer 112.

In some of the embodiments given above where the adhesive layer(s) 116, 122 are in direct contact with the indicator layer 112. Where appropriate, for these embodiments the ordering of the substrate layer 114 and the indicator layer 112 can be swapped such that the indicator material of the indicator layer 112 is not in direct contact with the adhesive in the adhesive layer(s) 116, 122. This can be of benefit as in some instances the adhesive will react with the indicator material, which can prevent the indicator device 110 from working, or which can cause the indicator device 110 to work in a suboptimal or unpredictable way.

Depending on the intended use of the indicator device 110, a first portion 128 of the indicator layer 112 may comprise the indicator material after exposure to chosen atmospheric conditions, and the second portion 126 may comprise the indicator material before exposure to chosen atmospheric conditions or vice versa.

For example, the indicator material may be chosen to detect carbon dioxide in modified atmosphere packaging, wherein the packaging contains carbon dioxide. In this case, the carbon dioxide used in the packaging process changes the colour of the indicator material. When the package is opened, the carbon dioxide is released, and the reference sections 126, which are not covered by a barrier layer 120, change colour to give a reference colour. Carbon dioxide is then gradually released from the section 128 including an indicator material, through the barrier layer 120, over a set period of time, gradually returning to the same colour as the reference sections 126. In an alternative embodiment the reference sections 126 are printed with any ink that is the same (or a very similar) colour as the section 128 including the indicator material after carbon dioxide has been released. In this embodiment the barrier layer 120 may cover the reference sections 126.

Alternatively, the indicator material may be chosen to detect oxygen in modified atmosphere packaging, wherein the packaging contains carbon dioxide. In this case, the carbon dioxide used in the packaging process does not change the colour of the indicator material, but the indicator layer 112 is in the non-oxidised (i.e., reduced) state. When the package is opened, the carbon dioxide is released, and oxygen can access the indicator layer, quickly changing the colour of the indicator material in the reference sections 126, which are not covered by a barrier layer 120, to give a reference colour. Oxygen then gradually accesses the section 128 including an indicator material, and covered by the barrier layer 120, over a set period of time, gradually returning to the same colour as the reference sections 126. In an alternative embodiment the reference sections 126 are printed with any ink that is the same (or a very similar) colour as the section 128 including the indicator material after exposure to oxygen. In this embodiment the barrier layer 120 may cover the reference sections 126.

In a variation of the above, the reference sections 126 may be exposed to oxygen prior to the packaging 500 being sealed, such that they show a different colour (a reference colour) to the section 128 including an indicator material.

In any event, at least one of the first 128 and second 126 portions acts as a reference section, and that reference can be the indicator material either before or after exposure to the atmospheric agent to which it is sensitive. Similarly, the section 128 at which a colour change is observed over time by the user, may comprise indicator material either before or after exposure to the atmospheric agent to which it is sensitive.

It will be appreciated that as described above the central section 128 may act as an indicator, and the outer section(s) 126 may act as a reference, or vice versa.

Figure 9:
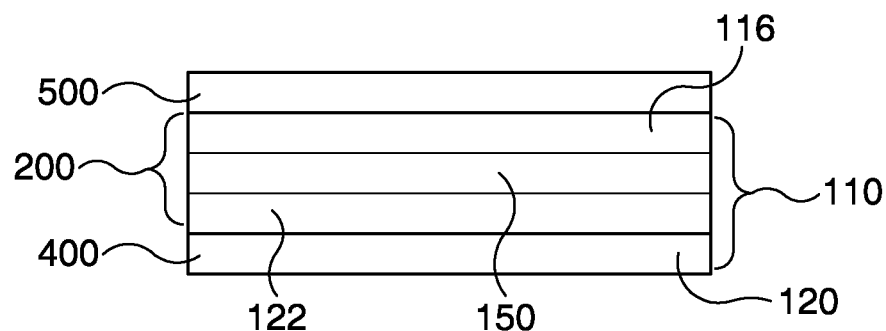
FIG. 9 is a cross section of one embodiment of the invention wherein a laminated sticker is applied to the inside of packaging, and wherein the laminated sticker has a combined substrate and indicator layer.

Referring now to FIG. 9, there is provided at 110 an indicator device in accordance with one embodiment of the invention, and attached to packaging material 500. The indicator device 110 has an indicator section 200 situated between the packaging 500 and a barrier section 400, and in contact therewith. The indicator section 200 consists of a polyethylene and silica combined indicator and substrate layer 150 located between an acrylic adhesive layer 116 and a further adhesive layer 122. It will be understood that the adhesive layer 122 could also be located in the barrier section 400. The barrier section 400 contains a low density polyethylene, polyester or polypropylene barrier layer 120.

The indicator device 110 is attached to packaging 500, such that the combined indicator and substrate layer 150 is visible to a user through the packaging 500. The indicator device 110 is constructed and located in such a way that selected atmospheric species (e.g., carbon dioxide, oxygen, water and ammonia) can reach the combined indicator and substrate layer 150, via the barrier layer 120. The barrier layer 120 may be selected such that it is "food safe". That is to say that it is made from a material approved for use next to foodstuffs.

Figure 10:
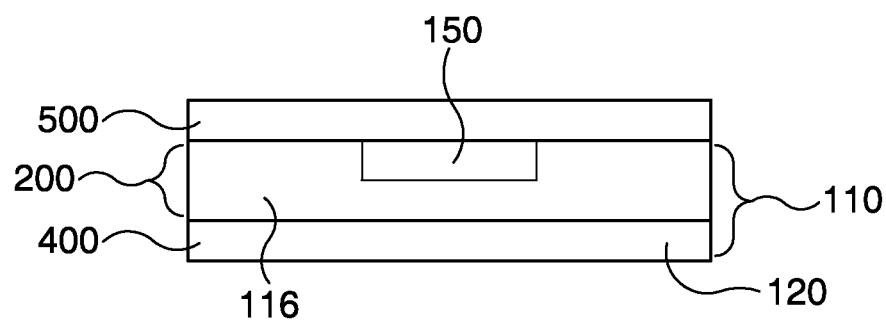
FIG. 10 is a cross section of an alternative embodiment of the invention wherein a laminated sticker is applied to the inside of packaging, and wherein the laminated sticker has a combined substrate and indicator layer.

Referring now to FIG. 10, there is provided at 110 an indicator device in accordance with one embodiment of the invention, and attached to packaging material 500. The indicator device 110 has an indicator section 200 situated between the packaging 500 and a barrier section 400, and in contact therewith. The indicator section 200 consists of a polyethylene oxide and alumina combined indicator and substrate layer 150 (which contains an indicator material as described above) and an acrylic adhesive layer 116. The acrylic adhesive layer 116 also covers the sides of the combined indicator and substrate layer 150. The barrier section 400 contains a low density polyethylene, polyester or polypropylene barrier layer 120. The combined indicator and substrate layer 150 is smaller in diameter than the barrier layer 120, the barrier layer 120 in combination with the adhesive layer 116 effectively acting as a "cap", which encapsulates the combined indicator and substrate layer 150, and affixes it to the packaging 500. It will be understood that the adhesive layer 116 could also be located in the barrier section 400.

The indicator device 110 is attached to packaging 500, such that the combined indicator and substrate layer 150 is visible to a user through the packaging 500. The indicator device 110 is constructed and located in such a way that selected atmospheric species (e.g., carbon dioxide, oxygen, water and ammonia) can reach the combined indicator and substrate layer 150, via the barrier layer 120. The barrier layer 120 may be selected such that it is "food safe". That is to say that it is made from a material approved for use next to foodstuffs.

Figure 11:
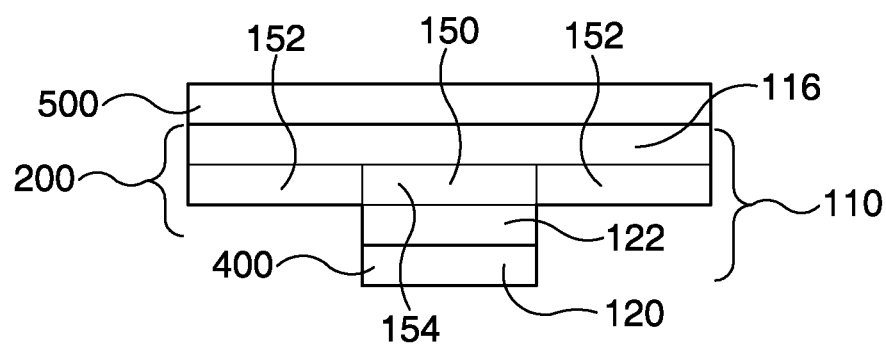
FIG. 11 is a cross section of a further embodiment of the invention wherein a laminated sticker is applied to the inside of packaging, and wherein the laminated sticker has a combined substrate and indicator layer.

Referring now to FIG. 11, there is provided at 110 an indicator device in accordance with one embodiment of the invention, and attached to packaging material 500. The indicator device 110 has an indicator section 200 situated between the packaging 500 and a barrier section 400, and in contact therewith. The indicator section 200 consists of a combined indicator and substrate layer 150 located between an acrylic adhesive layer 116 and a further adhesive layer 122. It will be understood that the adhesive layer 122 could also be located in the barrier section 400. The combined indicator and substrate layer 150 is split into sections, the central section 154 including an indicator material, and the outer section(s) 152 including a reference material. The barrier section 400 contains a low density polyethylene, polyester or polypropylene barrier layer 120. The barrier section 400 and barrier layer 120 cover only the central section 154 including an indicator material, and not the outer section(s) 152 including a reference material.

The indicator device 110 is attached to packaging 500, such that the combined indicator and substrate layer 150 is visible to a user through the packaging 500. The indicator device 110 is constructed and located in such a way that selected atmospheric species (e.g., carbon dioxide, oxygen, water and ammonia) can reach the indicator layer 112, via the barrier layer 120. The barrier layer 120 may be selected such that it is "food safe". That is to say that it is made from a material approved for use next to foodstuffs.

Depending on the intended use of the indicator device 110, a first portion 154 of the combined indicator and substrate layer 150 may comprise the indicator material after exposure to chosen atmospheric conditions, and the second portion 152 may comprise the indicator material before exposure to chosen atmospheric conditions or vice versa.

For example, the indicator material may be chosen to detect carbon dioxide in modified atmosphere packaging, wherein the packaging contains carbon dioxide. In this case, the carbon dioxide used in the packaging process changes the colour of the indicator material. When the package is opened, the carbon dioxide is released, and the reference sections 152, which are not covered by a barrier layer 120, change colour to give a reference colour. Carbon dioxide is then gradually released from the section 154 including an indicator material, through the barrier layer 120, over a set period of time, gradually returning to the same colour as the reference sections 152. In an alternative embodiment the reference sections 126 are printed with any ink that is the same (or a very similar) colour as the section 128 including the indicator material after carbon dioxide has been released. In this embodiment the barrier layer 120 may cover the reference sections 126.

Alternatively, the indicator material may be chosen to detect oxygen in modified atmosphere packaging, wherein the packaging contains carbon dioxide. In this case, the carbon dioxide used in the packaging process does not change the colour of the indicator material, but the combined indicator and substrate layer 150 is in the non-oxidised (i.e., reduced) state. When the package is opened, the carbon dioxide is released, and oxygen can access the indicator layer, quickly changing the colour of the indicator material in the reference sections 152, which are not covered by a barrier layer 120, to give a reference colour. Oxygen then gradually accesses the section 154 including an indicator material, and covered by the barrier layer 120, over a set period of time, gradually returning to the same colour as the reference sections 152. In an alternative embodiment the reference sections 126 are printed with any ink that is the same (or a very similar) colour as the section 128 including the indicator material after exposure to oxygen. In this embodiment the barrier layer 120 may cover the reference sections 126.

In a variation of the above, the reference sections 152 may be exposed to oxygen prior to the packaging 500 being sealed, such that they show a different colour (a reference colour) to the section 154 including an indicator material.

In any event, at least one of the first 154 and second 152 portions acts as a reference section, and that reference can be the indicator material either before or after exposure to the atmospheric agent to which it is sensitive. Similarly, the section 154 at which a colour change is observed over time by the user, may comprise indicator material either before or after exposure to the atmospheric agent to which it is sensitive.

It will be appreciated that as described above the central section 154 may act as an indicator, and the outer section(s) 152 may act as a reference, or vice versa.

Figure 12:
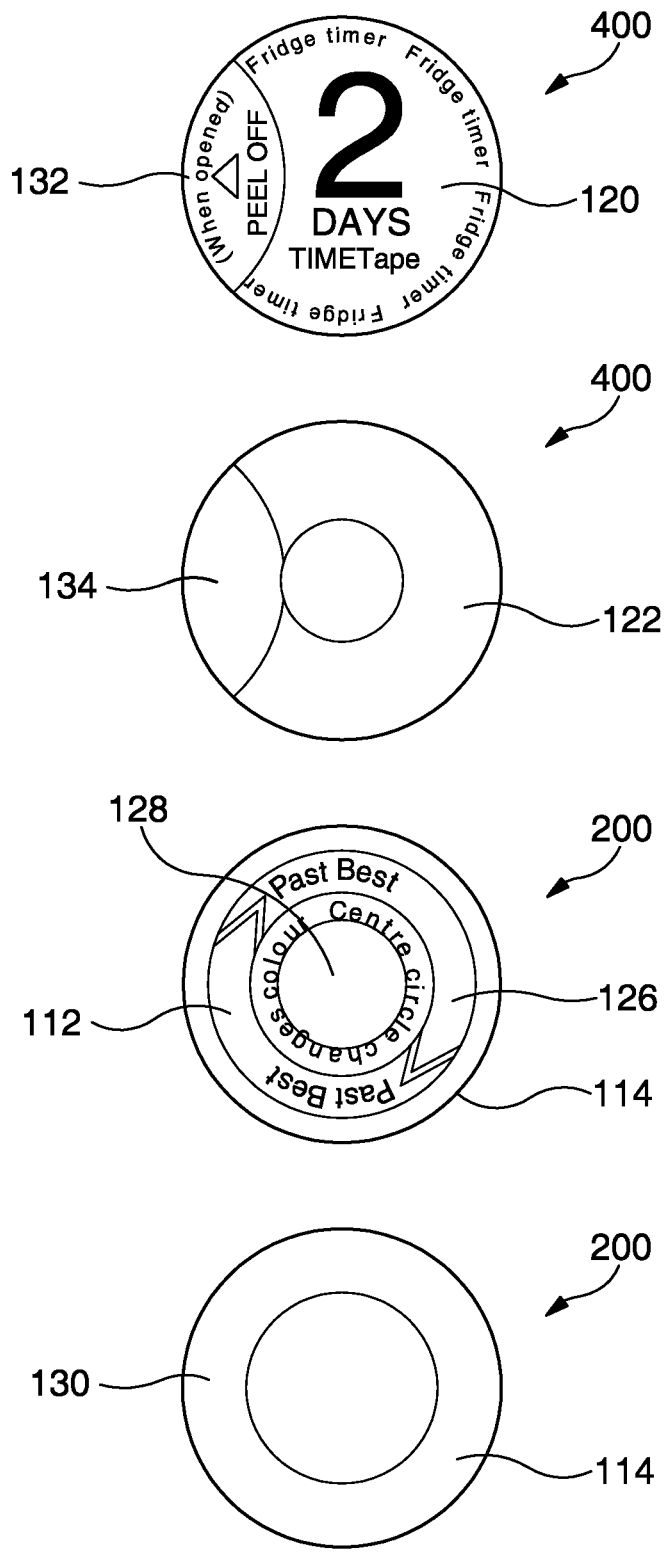
FIG. 12 is an exploded plan view of one embodiment of the indicator device.

Referring now to FIG. 12, there is provided an indicator device (sticker) in exploded plan view. The sticker has a top peel off section 400 which has two layers, and which acts as a barrier. One layer is printed such that there is a peelable section 120 and a tab 132 for gripping by the user. The other layer has a killed adhesive section 122 and a non-adhesive section 132.

The sticker also has a bottom indicator section 200 which has an indicator layer 112 printed on a polypropylene substrate 114, which includes a reference ink 126 and a redox active ink 128. There is a further layer (which may be on the same plane as the inks 126, 128) which incorporates a silicone polymer, which aids release of the top peel off section 400.

In use the user grips the tab 132, and pulls the top peel off section 400 off the bottom indicator section 200, thus the peelable section 120 and the adhesive section 122 are removed from the indicator section 200 to expose the indicator layer 112.

Note that silicone or silicon additives may be included in the inks or indicator payer to make any adhesive applied thereto easier to remove.

Figure 13:
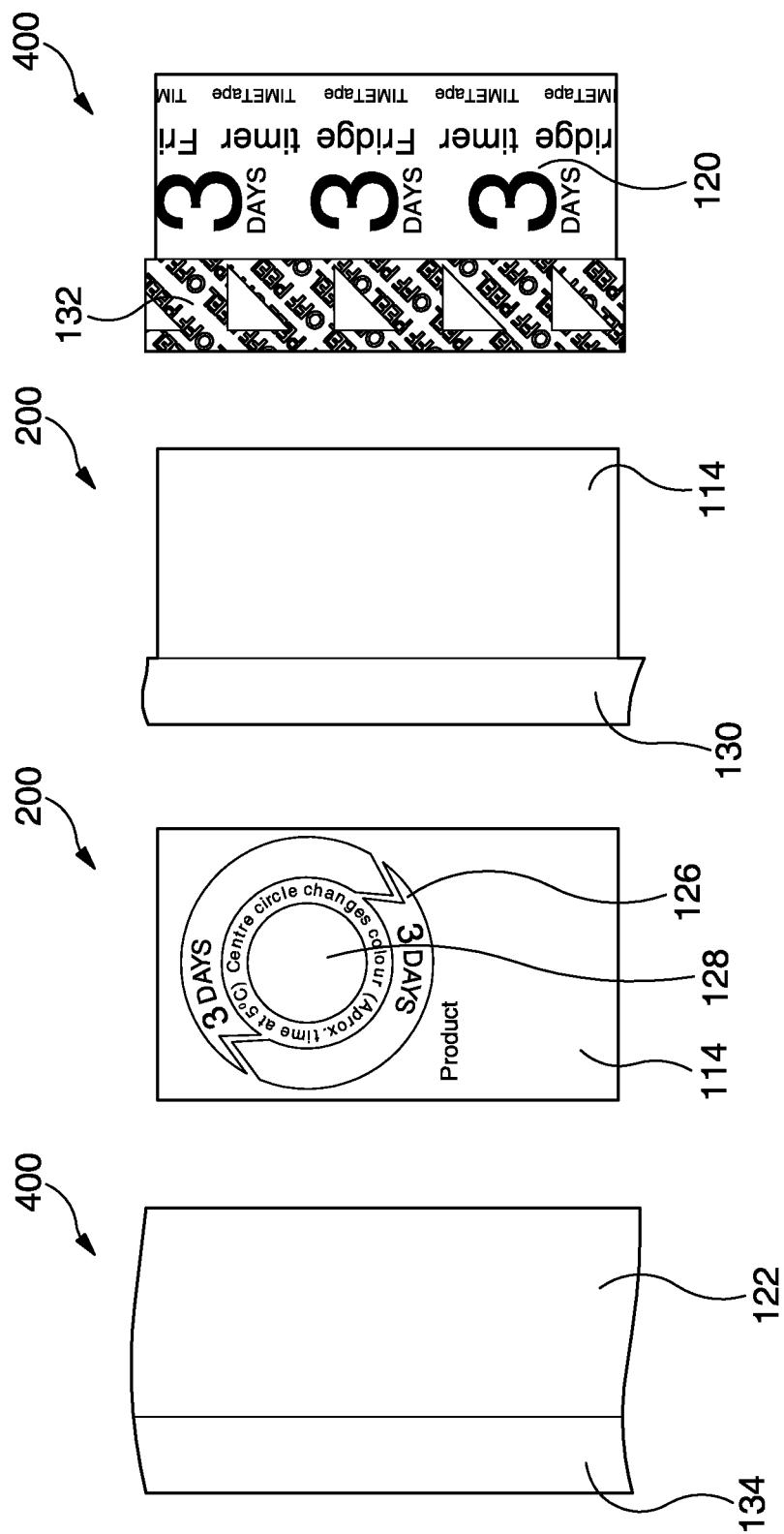
FIG. 13 is an exploded plan view of an alternative embodiment of the indicator device.

Referring now to FIG. 13 there is provided an indicator device (sticker) in exploded plan view. The sticker has a top peel off section 400 which has two layers, and which acts as a barrier. One layer is printed such that there is a peelable section 120 and a tab 132 for gripping by the user. The other layer has a killed adhesive section 122 and a non-adhesive section 132.

The sticker also has a bottom indicator section 200 which has an indicator layer 112 printed on a polypropylene substrate 114, which includes a reference ink 126 and a redox active ink 128. There is a further layer (which may be on the same plane as the inks 126, 128) of a silicone polymer, which aids release of the top peel off section 400.

In use the user grips the tab 132, and pulls the top peel off section 400 off the bottom indicator section 200, thus the peelable section 120 and the adhesive section 122 are removed from the indicator section 200 to expose the indicator layer 112.

Note that silicone or silicon additives may be included in the inks or indicator payer to make any adhesive applied thereto easier to remove.

Figure 14:
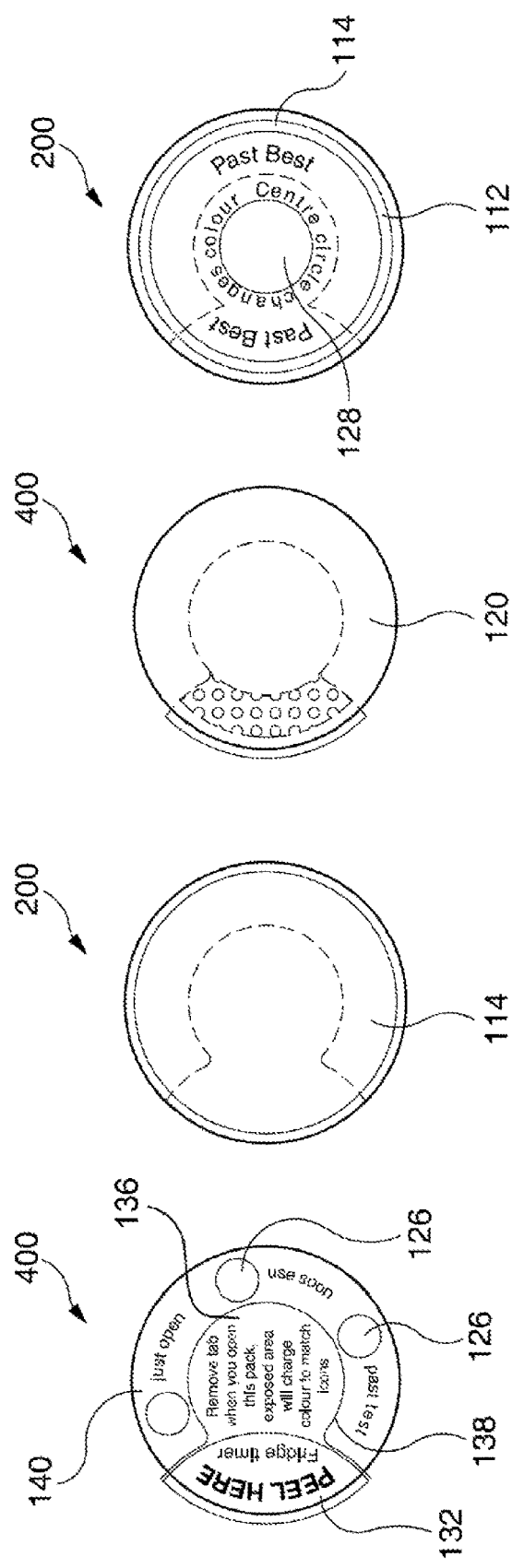
FIG. 14 is an exploded plan view of a further alternative embodiment of the indicator device.

Referring now to FIG. 14 there is provided a further alternative indicator device (sticker) in exploded plan view. The sticker has a top peel off section 400 which acts as a barrier, and which has a barrier layer 120, at least part of which is peelable. There is a peelable section 136, a tab 132 for gripping by the user, and an outer section 140. There is a frangible area 138 which enables the peelable section 136 to be removed, leaving behind part of the outer section 140. Printed onto the outer section 140 of the barrier layer 120 is a reference ink 126.

The sticker also has a bottom indicator section 200 which has an indicator layer 112 printed on a polypropylene substrate 114, which includes a redox active ink 128. The tab 132 is attached to the substrate 114 using an adhesive (bot shown).

In use the user grips the tab 132, and pulls the peelable section 136 from the outer section 140, breaking the barrier layer at the frangible area 138, thus revealing the bottom indicator section 200 and exposing the indicator layer 112, specifically the redox active ink 128.

In use the indicator device 110 is applied to the inside of a transparent layer of a package (for example, the transparent cover often applied to MAP packaged perishable foodstuffs such as cheese and meat) in the form of a "window sticker". The barrier section 400 of the indicator device 110 remains in place, and allows the controlled ingress of oxygen and/or water to the indicator layer. The release section 300 is removed and the adhesive 116 of the indicator section 200 is used to attach the indicator device 110 (minus the release section 300) to the inside of the packaging.

The ink layer 112 of the indicator device 110 is typically reverse printed on the polyethylene terephthalate substrate layer 114, so that when applied to the inside of transparent packaging, the design of the ink layer 112 appears in the correct orientation and position.

Figure 15:
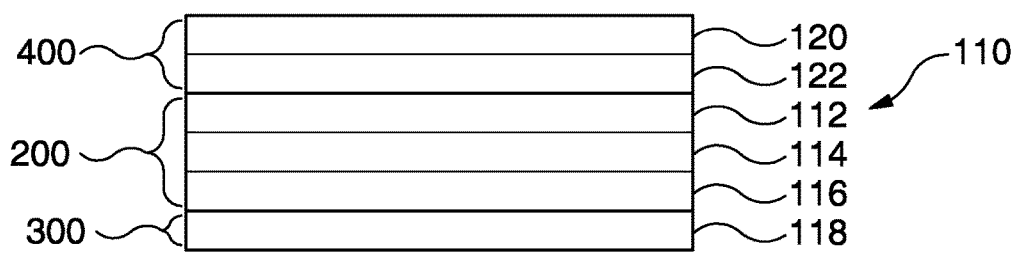
FIG. 15 is a cross section of a further embodiment of the device with a barrier layer, but without a semi-permeable barrier layer.

Referring now to FIG. 15, there is provided at 110 an indicator device in accordance with one embodiment of the invention. The indicator device 110 has an indicator section 200 situated between a release section 300 and a barrier section 400, and in contact therewith. The indicator section 200 consists of a polyethylene substrate layer 114 located between an indicator layer 112 (which contains the ink as described above) and a permanent adhesive layer 116. The barrier section 400 contains a clear polyethylene barrier layer 120 located next to an acrylic adhesive layer 122. It will be understood that the adhesive layer 122 could also be located in the indicator section, adjacent the barrier section 400. The release section 300 contains a glassine release layer 118 (also known as a release liner).

The indicator section 200 is located between the release section 300 and the barrier section 400. The indicator section 200 and the release section 300 are arranged so that the adhesive layer 116 is in contact with the release layer 118. The release layer 118 protects the adhesive layer 116 until such time that the indicator device 110 is to be attached to an item. The indicator section 200 and the barrier section 400 are arranged so that the indicator layer 112 is in contact with the adhesive layer 122 of the barrier section 400. The barrier section 400 protects the indicator layer 112 until a time that a user wishes to activate the indicator, which is done by removing the barrier layer 400.

Figure 16:
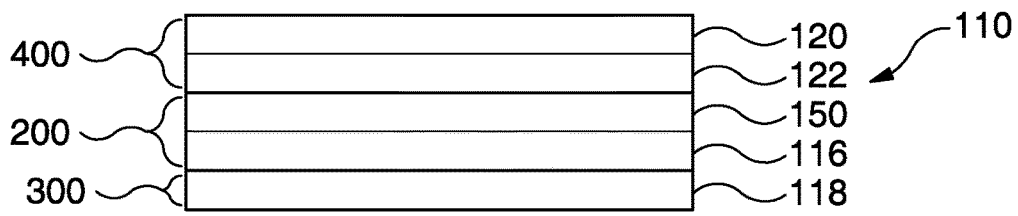
FIG. 16 is a cross section of an alternative embodiment of the device with a barrier layer, but without a semi-permeable barrier layer.

Referring now to FIG. 16, there is provided at 110 an indicator device in accordance with one embodiment of the invention. The indicator device 110 has an indicator section 200 situated between a release section 300 and a barrier section 400, and in contact therewith. The indicator section 200 consists of a polyethylene and silica combined indicator and substrate layer 150 located next to a permanent adhesive layer 116. The barrier section 400 contains a clear polyethylene barrier layer 120 located next to an acrylic adhesive layer 122. It will be understood that the adhesive layer 122 could also be located in the indicator section, adjacent the barrier section 400. The release section 300 contains a glassine release layer 118 (also known as a release liner).

The indicator section 200 is located between the release section 300 and the barrier section 400. The indicator section 200 and the release section 300 are arranged so that the adhesive layer 116 is in contact with the release layer 118. The release layer 118 protects the adhesive layer 116 until such time that the indicator device 110 is to be attached to an item. The indicator section 200 and the barrier section 400 are arranged so that combined indicator and substrate layer 150 is in contact with the adhesive layer 122 of the barrier section 400. The barrier section 400 protects the combined indicator and substrate layer 150 until a time that a user wishes to activate the indicator, which is done by removing the barrier layer 400.

Figure 17:
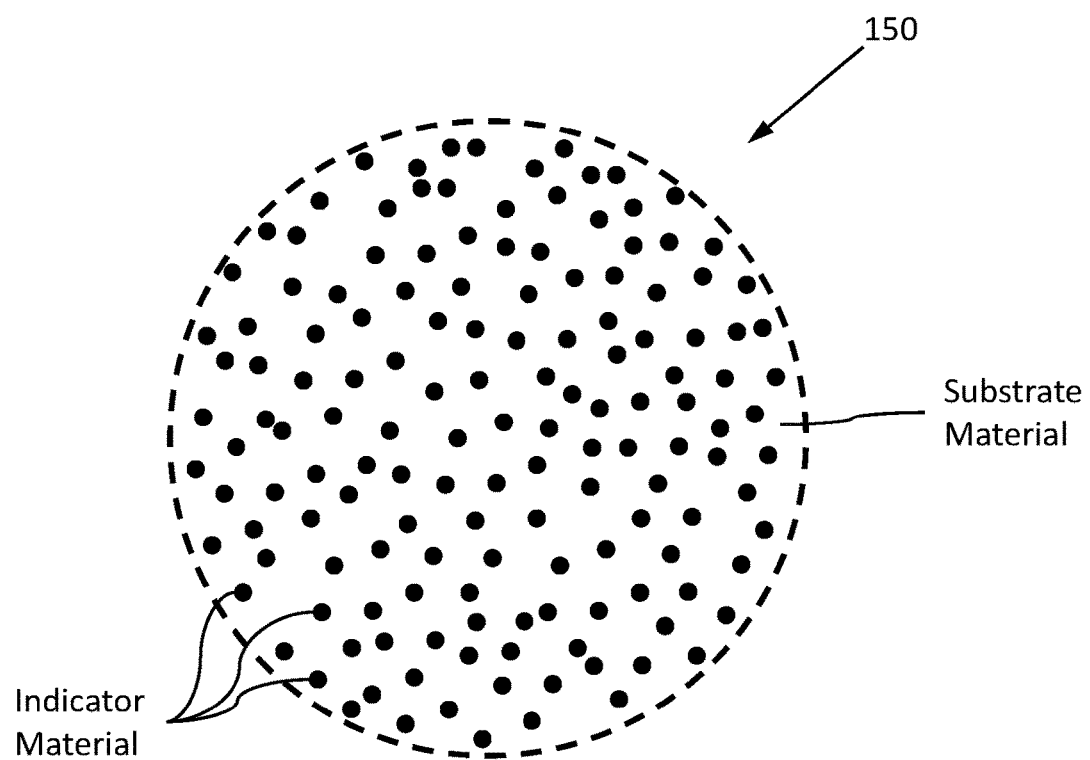
FIG. 17 is a detail view of one embodiment of a combined indicator and substrate layer 150.

Referring now to FIG. 17, there is provided a combined indicator and substrate layer 150. The combined indicator and substrate layer 150 may include an indicator material dispersed within a substrate material.

The indicator layer or combined indicator and substrate layer may include a chemical agent that cause a colour change to the active component (i.e., indicator material) therein. As examples, the chemical agent can be an oxidising agent, water, carbon dioxide, amines, ammonium hydroxide or ammonia.

For example, if the active component is reactive to the presence of amines and the like, the chemical agent could be from one or more of ammonia, ammonium hydroxide, propylamine, butylamine, hexylamine and octylamine.

In use, the barrier layer is removed and the concentration of the chemical agent in the indicator section changes over time, effecting a change in visible properties of the indicator material. Specifically in one embodiment on removal of the removable barrier layer, the concentration of the chemical agent in the indicator layer/indicator layer decreases over time. This may take place by a process of diffusion out of the indicator section/indicator layer.

The substrate layer typically has a thickness of between 50 μm and 100 μm. Alternative substrates that can be used include aluminium oxide foil, polypropylene, and polyethylene terephthalate; and platinised versions thereof.

The indicator layer typically has a thickness between 1 μm and 3 μm.

Alternative indicators that can be used include a redox sensitive material, a carbon monoxide sensitive material, a carbon dioxide sensitive material, an oxygen sensitive material and an ammonia sensitive material.

The barrier layer has a thickness of between approximately 12 μm and 300 μm, typically between 30 μm and 200 μm. Alternative barrier layers that can be used include polyethylene terephthalate, ethylene vinyl alcohol, polyvinylidene chloride, polyvinyl alcohol, low density polyethylene, polypropylene, polyester and aluminium oxide coated polyethylene terephthalate.

The coating layer typically has a thickness of between approximately 1 μm and 3 μm. Alternative coating layers that can be used include polyethylene terephthalate, ethylene vinyl alcohol, polyvinylidene chloride, polyvinyl alcohol and aluminium oxide coated polyethylene terephthalate.

The adhesive layer typically has a thickness between 1 μm and 3 μm. Alternative adhesives that can be used include a rubber based hot melt, an acrylic adhesive, a varnish coated adhesive, an adhesive kill treated adhesive, a treated or coated permanent acrylic, and a treated or coated peelable acrylic.

The release layer may be approximately 50 μm to 100 μm, and is typically between 60 μm and 70 μm. Alternative release layers that can be used include glassine, siliconised glassine paper, and a silicon treated polymer.

The indictor devices as illustrated in FIGS. 1 and 2 are prepared as follows. A supported 50 μm polypropylene substrate 114 having an acrylic adhesive layer 116 and a standard silicone release liner 118, is introduced to a standard flexographic printing press as is known in the art. The ink layer 112 is then printed onto the polypropylene 114.

The desired design and shape is then cut out using a die cutter and excess material is removed. The so-produced indicator device 110 (containing labels) is reverse wound to protect the indicator layer 112 from contact with the atmosphere, and in particular oxygen. The indicator device 110 is stored in refrigerated conditions.

In one embodiment, the ink layer 112 is divided into vertical sections (not shown) which contain a reference ink, which is first printed onto the polypropylene substrate 114, and a redox active ink as described. The reference ink can be UV cured, or may be allowed to dry naturally before printing of the redox active ink which is dried using hot air blowers.

The indictor device as illustrated in FIG. 3 is prepared as follows. A supported 50 μm polypropylene substrate/barrier 120 having an acrylic adhesive layer 122 and a standard silicone release liner is introduced to a standard flexographic printing press as is known in the art. The release liner is removed and material is brought out of the press using a turning bar. The adhesive layer 116 is then printed with a UV curing varnish which "kills" the adhesive. "Killing" the adhesive means to decrease the tack of the adhesive. Thus there is provided a barrier section 400. The barrier section 400 can be further supplemented by a coating layer (not shown) of the type described herein.

A further portion of supported 50 µm polypropylene substrate 114 having an acrylic adhesive layer 116 and a standard silicone release liner 118, is introduced to the flexographic printing press. A partial layer of reference ink 126 is printed on the substrate 114, and a partial layer of silicone polymer 130 is printed on top of the reference ink 126. An active ink 128 is then printed on a section of the substrate 114, which is free from reference ink 126 and silicone polymer 130. Thus there is provided an indicator section 200. The silicone release liner 118 provides a release section 300.

The barrier section 400 and the indicator section 200 are then brought together to provide a laminate, the adhesive layer 122 of the barrier section 400 being applied to the indicator layer 112 of the indicator section 200. If desired, a further design/ink can then be printed on top of the barrier layer 120 of the barrier section 400. The indicator device 110 is stored in refrigerated conditions.

The indictor device as illustrated in FIG. 4 is prepared as follows. A supported 50 µm polypropylene substrate 114 having an acrylic adhesive layer 116 and a standard silicone release liner 118 is introduced to a standard flexographic printing press as is known in the art. A partial layer of reference ink 126 is printed on top of the substrate 114, using a UV curing or water based ink. A partial layer of patterned adhesive 122 is then printed on top of the reference ink 126. An active ink 128 is then printed on a section of the substrate 114, which is free from reference ink 126 and adhesive 122, and dried using hot air blowers. Typically the reference ink 126 is coloured such that it is same hue as the redox active ink 128 when it is oxidised. An unsupported polyethylene terephthalate film 120 is then laminated to the adhesive layer 122. A further design can optionally be printed on top of the barrier layer 120.

Thus there is provided an indicator device 110 having an indicator section 200 comprising an adhesive layer 122, which attaches to a barrier layer 120, which acts as a barrier section 400. The silicone release liner 118 provides a release section 300.

The indicator device 110 is then die cut, and the excess tape is removed. The tape/stickers so produced can then be made into rolls or arranged on sheets.

The indictor device as illustrated in FIG. 5 is prepared as follows. A supported 50 µm polypropylene substrate 114 having an acrylic adhesive layer 116 and a standard silicone release liner 118 is introduced to a standard flexographic printing press as is known in the art. A partial layer of reference ink 126 is printed on top of the substrate 114, using a UV curing or water based ink. An active ink 128 is then printed on a section of the substrate 114, which is free from reference ink 126, and is dried using hot air blowers. Typically the reference ink 126 is coloured such that it is same hue as the redox active ink 128 when it is oxidised.

An unsupported polyethylene terephthalate film 120 is reverse printed with a "killed" adhesive 122 to form a barrier section 400, which is then laminated to the indicator layer 112. A further design can optionally be printed on top of the barrier layer 120. A "killed" adhesive is used to stop the adhesive layer 122 from reacting with the ink layer 112 (specifically the redox active ink 128) which it is in contact with. Alternatively, or in addition, a patterned adhesive can be used in which the pattern is designed and printed such that there is no adhesive printed on the section that comes into contact with the redox active ink.

Thus there is provided an indicator device 110 having an indicator section 200, which attaches to a barrier layer 120, which comprises an adhesive layer 122, and which acts as a barrier section 400. The silicone release liner 118 provides a release section 300.

The indicator device 110 is then die cut, and the excess tape is removed. The tape/stickers so produced can then be made into rolls or arranged on sheets.

In one embodiment, the indicator device 110 is arranged in a spiral such that the outermost layer of the spiral is the release layer 118, thus protecting the indicator layer 112 from exposure to air. Alternatively, the indicator device 110 may be arranged in a spiral such that the outermost layer of the spiral is the indicator layer 112, in which case the outermost layer of indicator is exposed to air and therefore will change colour, but the remaining layers of indicator device 110 will remain protected. These embodiments are usefully employed when the indicator device 110 does not have a barrier section 400, a barrier layer 120 or a coating layer 124.

Substrate layers that can be used in conjunction with or as a replacement for those specified above include aluminium foil, aluminium oxide foil, polyethylene terephthalate and/or polypropylene.

The substrate layer, adhesive layer and/or the indicator layer may include platinum. Platinum can be used to catalyse (and therefore speed up) the reduction of the indicator.

The indicator devices of FIGS. 6 to 11 are prepared substantially as described above for the indicator devices of FIGS. 1 to 5.

In one embodiment the indicator device is an oxygen indicator for informing a user when a food stuff or the like is no longer fresh, or no longer considered to be fit for consumption. The indicator layer may be displayed as a dot or a cross inside a coloured ring (a reference section). When the dot or a cross changes colour to the extent that it is the same colour as (or optionally darker) than the ring, the product is no longer fit for consumption. Alternatively, the indicator layer may be displayed as a tick inside a differently coloured ring (a reference section). When the tick is a different colour to the ring, the product is fit for consumption, but when the tick is substantially the same colour as the ring, the product is no longer fit for consumption. A similar arrangement can be used in alternative embodiments (optionally by utilising different dyes), which are useful in detecting whether packages have been opened, whether unopened food is no longer fit for consumption, or whether devices have been exposed to water, for example.

The indicator device can be printed on to the reverse side of an oxygen barrier film. Another film, which is oxygen permeable can be applied such that the ink is sandwiched between the two films. The oxygen permeable film delays the ingress of oxygen to the indicator, and thus increases the amount of time taken for the indicator to change colour. Various reference colours can be placed next to the indicator such that the freshness of the item to which the indicator is applied can be determined. Depending on whether the indicator device is placed inside or outside the packaging, this can be used to determine if a package has been inadvertently opened, to determine how long a package has been opened for, or to establish for how long a package has been stored.

The indicator device of the present invention can be used as a "best before" type indicator as follows. The indicator device is applied to the outside of food or drink packaging by those packaging food (for example, in an in-store bakery or butchers in a supermarket). The indicator layer is activated at the same time as, or just after, application to the packaging. A seal or barrier can be used to delay the colour change of the indicator layer, although this is not always necessary. For example, a suitable varnish or oxygen barrier material can be combined with the ink to delay the colour change.

The indicator device can therefore be used as a visual indicator to indicate to staff working in a supermarket that goods are nearing, or beyond, the best before date. This will allow staff to quickly identify such goods, thus allowing them to mark them for reduction, or to otherwise dispose of them.

In a further embodiment, the indicator device is used to indicate when a "consume within a certain time from opening" period has passed. Such periods vary from a few days to several months depending on the nature of the perishable item. The indicator device can, for example, be applied to the inside of vacuum or controlled atmosphere packaging (thus keeping the indicator device free from exposure to oxygen). When the packaging is opened, the indicator device will be exposed to oxygen and will change colour over a set period of time.

Alternatively, the "consume within" indicator device can be applied to the outside of packaging along with a seal or barrier layer (if, for example, the oxygen content inside the packaging is too high for the indicator to remain clear). When the packaging is opened, the seal or barrier is removed allowing the indicator layer to be exposed to the atmosphere. The indicator layer will then change colour over a set period of time.

In one embodiment the indicator device is incorporated into a water indicator for informing a user when an item has been exposed to moisture. The indicator device can be applied to the inside of moisture sensitive goods in substantially moisture-free packaging such as dried foods, electrical equipment and pharmaceuticals. If the packaging is compromised, moisture will enter the package and the indicator layer will change colour thus indicating to the end consumer that the goods that they have received have not been in the required atmospheric conditions and therefore may be spoiled or damaged. In this embodiment, the indicator device can also be used to warn manufacturers or distributors that their goods are being exposed to moisture, and that they may need re-packaged, or that they may not be fit for sale.

In one embodiment the indicator device is incorporated into a time-temperature indicator. Oxidation (but seemingly not reduction) of the indicator composition is temperature sensitive. Once activated, the reduced composition will remain clear if kept at typical domestic freezer temperatures (less than −20° C.). Therefore, the indicator device can be used to demonstrate when frozen items have been subject to an increase in temperature. For example, the indicator device can be applied to a frozen foodstuff. If the item defrosts, the indicator layer will change colour, thereby illustrating that the item has been at too high a temperature. If the item is re-frozen, the indicator remains coloured. This can be useful for the consumer, the manufacturer, the distributor and the seller. In particular, the time temperature indicator device can be useful for frozen seafood, frozen dairy products (such as ice cream), and frozen poultry, all of which are associated with exponential bacterial growth when exposed to high temperatures (particularly when subsequently re-frozen and defrosted).

If the label is to be used in a conventional freezer, with normal moisture levels, it is recommended that a barrier layer/section is included specifically to mitigate, or at least slow, the ingress of water to the indicator section/layer. This layer may comprise polyethylene, and specifically may be a thin (or very thin) polyethylene layer. Such a barrier may not be necessary in a dry freezer, which has much lower moisture levels.

In a further embodiment, the indicator device comprises a barrier layer or section configured to prevent, mitigate or slow the action of UV light on the indicator layer or section.

In a yet further embodiment, the indicator device is incorporated into an anti-counterfeiting device.

The indicator device can be applied to the inside of substantially air-free and/or substantially oxygen-free packaging for high value, or often counterfeited goods. When the packaging is opened, a logo or message appears indicating that the goods are genuine. The logo or message can be verified further by applying UV light, which will make the logo or message disappear. The logo or message would then reappear after a short period of time. This could, of course, also be applied to currency and/or documentation.

Examples of Indicator Device in Use

Four different types of indicator tape/sticker were tested to determine the period of time over which they changed colour at room temperature, and in a refrigerator. A control study was also carried out on an indicator tape/sticker which was taken from the inside of a roll of stickers, which had minimal access to air. The roll of stickers was stored at approximately 4° C. Each day a new control sticker was used, as the stickers used on previous days would thereafter be on the outside of the roll of stickers, and thus exposed to oxygen.

The types of sticker tested had the following substrate materials: polypropylene; platinised polypropylene; aluminium oxide foil; and platinised aluminium oxide foil. The stickers were all originally white to grey in colour and their recovery to a deep blue colour was monitored daily by diffuse reflectance spectroscopy using a hand-held Konica-Minolta CM-2500d Spectrophotometer. The tests were run over an eight day period.

The reflectance measurements taken were reported using the following readings and nomenclature, and using an instrument that emits D65 light (i.e., light that is related to daylight with the same amount of UV light as in a winter day):

L*, which is a measure of perceived lightness on a scale of 0 to 100;

a*, which is a measure of the hue on the red/green axis, where a positive value means red, and a negative value means green; and b*, which is a measure of the hue on the yellow/blue axis, where a positive value means yellow, and a negative value means blue.

Example 1—Polypropylene Substrate

TABLE 1.1

Recovery at room temperature

| Time (days) | L*(D65) | a*(D65) | b*(D65) |
| --- | --- | --- | --- |
| 1 | 93.27 | −2.65 | −0.89 |
| 2 | 89.06 | −10.48 | −6.18 |
| 3 | 85.81 | −14.21 | −9.27 |
| 6 | 83.10 | −16.17 | −12.00 |
| 7 | 82.27 | −16.61 | −12.31 |
| 8 | 82.04 | −16.23 | −11.93 |

TABLE 1.2

| | Recovery in refrigerator | | |
|---|---|---|---|
| Time (days) | L*(D65) | a*(D65) | b*(D65) |
| 1 | 93.27 | −2.65 | −0.89 |
| 2 | 92.21 | −5.83 | −1.83 |
| 3 | 90.21 | −9.46 | −4.88 |
| 6 | 85.16 | −15.43 | −10.80 |
| 7 | 83.70 | −16.33 | −12.32 |
| 8 | 83.50 | −16.42 | −12.48 |

TABLE 1.3

| | Control/reference in refrigerator | | |
|---|---|---|---|
| Time (days) | L*(D65) | a*(D65) | b*(D65) |
| 1 | 93.27 | −2.65 | −0.89 |
| 2 | 93.52 | −1.74 | 0.07 |
| 3 | 92.59 | −2.28 | −0.14 |
| 6 | 93.65 | −2.08 | 0.29 |
| 7 | 93.82 | −2.26 | 0.43 |
| 8 | 93.72 | −1.89 | 0.20 |

Example 2—Platinised Polypropylene Substrate

TABLE 2.1

| | Recovery at room temperature | | |
|---|---|---|---|
| Time (days) | L*(D65) | a*(D65) | b*(D65) |
| 1 | 92.25 | −3.73 | −0.78 |
| 2 | 86.72 | −12.85 | −7.14 |
| 3 | 84.57 | −15.47 | −9.99 |
| 6 | 81.05 | −17.85 | −13.91 |
| 7 | 80.65 | −18.07 | −14.15 |
| 8 | 80.33 | −17.87 | −14.53 |

TABLE 2.2

| | Recovery in refrigerator | | |
|---|---|---|---|
| Time (days) | L*(D65) | a*(D65) | b*(D65) |
| 1 | 92.25 | −3.73 | −0.78 |
| 2 | 90.27 | −6.30 | −2.84 |
| 3 | 88.03 | −10.43 | −6.54 |
| 6 | 84.59 | −15.23 | −10.66 |
| 7 | 81.97 | −16.94 | −13.35 |
| 8 | 82.23 | −17.05 | −13.54 |

TABLE 2.3

| | Control/reference in refrigerator | | |
|---|---|---|---|
| Time (days) | L*(D65) | a*(D65) | b*(D65) |
| 1 | 92.25 | −3.73 | −0.78 |
| 2 | 92.29 | −4.23 | 0.61 |
| 3 | 91.15 | −3.94 | −0.57 |
| 6 | 92.32 | −3.20 | −0.30 |
| 7 | 92.03 | −4.78 | 0.44 |
| 8 | 92.10 | −4.31 | 0.07 |

Example 3—Aluminium Oxide Foil Substrate

TABLE 3.1

| | Recovery at room temperature | | |
|---|---|---|---|
| Time (days) | L*(D65) | a*(D65) | b*(D65) |
| 1 | 85.21 | −1.53 | −1.17 |
| 2 | 80.51 | −11.02 | −7.57 |
| 3 | 77.83 | −14.71 | −10.71 |
| 6 | 74.58 | −17.11 | −13.41 |
| 7 | 74.48 | −16.29 | −13.05 |
| 8 | 74.43 | −16.17 | −12.94 |

TABLE 3.2

| | Recovery in refrigerator | | |
|---|---|---|---|
| Time (days) | L*(D65) | a*(D65) | b*(D65) |
| 1 | 85.21 | −1.53 | −1.17 |
| 2 | 84.18 | −4.31 | −2.80 |
| 3 | 82.03 | −8.27 | −4.83 |
| 6 | 78.26 | −14.44 | −10.14 |
| 7 | 77.20 | −15.68 | −11.77 |
| 8 | 76.21 | −16.10 | −12.62 |

TABLE 3.3

| | Control/reference in refrigerator | | |
|---|---|---|---|
| Time (days) | L*(D65) | a*(D65) | b*(D65) |
| 1 | 85.21 | −1.53 | −1.17 |
| 2 | 85.01 | −2.10 | −1.32 |
| 3 | 85.23 | −1.43 | −1.19 |
| 6 | 85.13 | −1.59 | −1.41 |
| 7 | 85.01 | −2.04 | −1.38 |
| 8 | 85.16 | −1.51 | −1.31 |

Example 4—Platinised Aluminium Oxide Foil Substrate

TABLE 4.1

| | Recovery at room temperature | | |
|---|---|---|---|
| Time (days) | L*(D65) | a*(D65) | b*(D65) |
| 1 | 84.34 | −2.50 | −1.07 |
| 2 | 78.61 | −13.46 | −8.69 |
| 3 | 76.12 | −16.38 | −11.35 |
| 6 | 73.28 | −18.21 | −14.53 |
| 7 | 72.82 | −18.31 | −14.95 |
| 8 | 72.73 | −18.05 | −14.83 |

TABLE 4.2

| | Recovery in refrigerator | | |
|---|---|---|---|
| Time (days) | L*(D65) | a*(D65) | b*(D65) |
| 1 | 84.34 | −2.50 | −1.07 |
| 2 | 83.36 | −4.23 | −2.38 |
| 3 | 81.85 | −8.04 | −4.88 |
| 6 | 78.83 | −13.35 | −8.51 |
| 7 | 77.84 | −14.66 | −10.03 |
| 8 | 77.63 | −14.62 | −10.09 |

TABLE 4.3

| Control/reference in refrigerator | | | |
| --- | --- | --- | --- |
| Time (days) | L*(D65) | a*(D65) | b*(D65) |
| 1 | 84.34 | −2.50 | −1.07 |
| 2 | 84.18 | −2.69 | −1.35 |
| 3 | 84.27 | −2.48 | −1.44 |
| 6 | 83.78 | −3.07 | −1.88 |
| 7 | 83.72 | −4.02 | −1.78 |
| 8 | 83.73 | −3.23 | −2.00 |

The indicator tape/stickers recovered faster at room temperature than in the refrigerator. The indicator tape/stickers stored in a roll showed little or no sign of recovery. The platinised substrates recover faster than the non-platinised equivalent, particularly at room temperature. The stickers having aluminium oxide foil substrates were a darker shade (grey) before the start of the experiments, and throughout the experiments. This is represented in the reflectance measurements recorded. All of the stickers placed in the refrigerator and kept at room temperature appeared to have fully recovered after approximately 7 to 8 days.

In the examples given, the barrier and coating layers of the barrier section are polyethylene terephthalate, polyethylene or ethylene vinyl alcohol. However, it will be appreciated that any suitable seal having a very low oxidising agent permeability (thereby preventing oxidation of the indicator) can be used in the barrier section. Alternatively, the barrier section materials may be chosen to provide a semi-permeable seal configured to allow controlled flow of oxidising agent to the indicator layer. Examples of suitable materials for use in the barrier section are polyethylene terephthalate (PET), ethylene-vinyl alcohol copolymer (EVOH), polyvinylidene chloride (PVDC), polyvinyl alcohol (PVA), polyethylene (PE) and low density polyethylene (LDPE). In a further alternative, the barrier layer may be chosen to mitigate, or at least slow, the ingress of water to the indicator layer or section. In a still further alternative, the barrier layer may be chosen to prevent, mitigate or slow the action of UV light on the indicator layer or section.

The rate of reaction between the reduced form of the redox dye, Red, and oxygen may be rendered mass-transfer dependent, by making the rate of diffusion of oxygen from the ambient air through the film the rate determining step.

The latter can be achieved by making the diffusion process very slow through the use of polymers with low oxygen permeability such as polyethylene terephthalate, either as the polymer encapsulating medium or as a film covering the indicator layer. Through the use of such a diffusion barrier it is possible to create a type of indicator film that exhibits a recovery time (when exposed to air) that depends upon the thickness of the diffusion barrier film; the thicker the oxygen barrier, the slower the film recovery. When used as an oxygen indicator, in an oxygen-free package, the colour recovery times of this type of indicator can be made sufficiently long (i.e. hours and/or days) that it can provide an indication of how long a modified atmosphere package has been opened, after it is opened and air allowed in.

If a very oxygen impermeable membrane is used as the barrier, the indicator is no longer sensitive towards oxygen and the degree of bleaching the film undergoes upon exposure to UV light can be used as a measure of the level of ambient UV light the film has been exposed to, i.e. such an indicator is a UV-light level indicator.

Further Examples of Indicator Devices in Use

Indicator devices were constructed using the combined indicator and substrate layer ("pigmented films") as described herein. The combined indicator and substrate layer comprised pigmented polyethylene (PE) film with a barrier layer of polymer film on top. The pigmented films change colour in response to the presence or absence of carbon dioxide, and is therefore useful in modified atmosphere packaging (MAP). Different types and thicknesses of polymer barrier were employed in order control the amount of time taken for the colour change to take place.

The pigmented films used to construct the indicator devices have a thickness of 50-60 μm and incorporated one of two different dyes: phenol red or m-cresol purple. Phenol red changes from yellow (when detecting presence of carbon dioxide dioxide) to purple (when not detecting presence of carbon dioxide) through an intermediate red colour. Typically, this colour change takes place once a package has been open for a set period of required time. An alternative dye, m-cresol purple, changes from yellow (when detecting presence of carbon dioxide dioxide) to blue (when not detecting presence of carbon dioxide) through a less distinct intermediate green colour. It will be appreciated that the pigmented film can be thicker or thinner than 50-60 μm and may, for example, be 70 μm.

Twenty-Four Hour Timer

A twenty-four hour timer was prepared with phenol red pigmented film covered with a barrier film of clear polyethylene terephthalate (PET) having a thickness of 12 μm as supplied by Smith and McLaurin (O/L PET 12/CP400/HG6). The package was charged with carbon dioxide, changing the indicator device from purple to yellow, and then the package was sealed. The package was then opened and within twelve hours the indicator device had turned red (intermediate colour). Within twenty-four hours, the package had turned purple, indicating that carbon dioxide was no longer present in the pigmented film. Therefore, this indicator device is useful in illustrating the passage of twenty-four hours' time.

Seventy-Two Hour Timer

A seventy-two hour timer was prepared with phenol red pigmented film covered with a barrier film of clear polyethylene terephthalate (PET) having a thickness of 36 μm as supplied by Smith and McLaurin (O/L PET clear 36/AT231/65HG). The package was charged with carbon dioxide, changing the indicator device from purple to yellow, and then the package was sealed. The package was then opened and within twenty-four hours the film had turned orange, and within forty-eight hours the indicator device had turned red (intermediate colour). Within seventy-two hours, the package had turned purple, indicating that carbon dioxide was no longer present in the pigmented film. Therefore, this indicator device is useful in illustrating the passage of seventy-two hours' time.

Alternative Seventy-Two Hour Timer

A seventy-two hour timer was prepared with m-cresol purple pigmented film covered with a barrier film of white polypropylene (PP) having a thickness of 150 μm as supplied by Smith and McLaurin (transfer PP150/SP8000/65HG). The package was charged with carbon dioxide, changing the indicator device from deep blue to yellow, and then the package was sealed. The package was then opened and within forty-eight hours the indicator device had turned green (intermediate colour). Within seventy-two hours, the package had turned deep blue, indicating that carbon dioxide was no longer present in the pigmented film. Therefore, this indicator device is also useful in illustrating the passage of seventy-two hours' time.

The indicator devices described herein are useful in the manufacture of "consume within" timers. Consume within timers are typically activated after a package is opened, and are used to indicate when a set period of time has elapsed since opening of the package, the foodstuff within the package having to be "consumed within" that set period of time. The indicator device will change colour once the set period of time has elapsed, thereby advising the user that the foodstuff should no longer be consumed. This helps to prevent consumption of unfit foods, and removes the need for users to try to recall when they first opened foodstuffs.

The thickness of barrier depends on the type of material being used, and the desired length of time for the colour change to take place. Less effective barrier materials typically require to be thicker than more effective barrier materials in order to achieve a particular time for the colour change to take place. Typically, the thicker a barrier becomes, the less flexible it is; this can cause problems in the printing process. For example, an inflexible thick barrier is more likely to peel off the packaging to which it has been applied if that packaging is run over an angled piece of machinery. However, if a barrier is too thin, then it may lack structural integrity and be caused to stretch during the printing process. Therefore, it will be appreciated that the choice of the type and thickness of barrier material is determined by many factors including: the desired length of time for the colour change, the permeability of the barrier to the agent to be detected and the structural properties of the barrier material.

An indicator device as described in FIG. 8 or 11 and sensitive to carbon dioxide was applied to packaging as follows. The indicator device was attached to inside surface of the transparent lid of the packaging, by way of the exposed or releasable adhesive layer of the indicator device. The packaging was then processed on a flow wrapping packaging line in the normal way, during which carbon dioxide was flushed into the packaging, thereby changing the indicator material to a colour which indicated that it had been exposed to carbon dioxide. The carbon dioxide content of the packaging was about 30% to about 40% by volume. The colour change takes place in matter of seconds, and therefore the indicator device is "activated" quickly and conveniently, without the need for any separate intervention or activation step.

The package was subsequently opened and the portions of the indicator/combined indicator and substrate section not covered by the barrier layer almost immediately changed colour, created a contrast between the portion covered by the barrier layer and the portion not covered by the barrier layer (the reference portion).

Over three days, carbon dioxide diffused out of the device through the barrier layer, the portion covered by the barrier layer gradually changing colour such that it eventually appeared the same colour as the reference portion. Note that the reference portion may be printed with any ink that is the same (or a very similar) colour to section including the indicator material after dissipation of carbon dioxide. In this embodiment the barrier layer may cover the reference section.

In the examples given, the indictor layer is applied using a printable ink and comprises: (i) methylene blue (a thiazine dyestuff); and (ii) either glycerol and nanorutile titanium (IV) oxide ($TiO_2$), or sodium dithionite (a reducing agent) and/or the oxidation products therefrom (thiosulphate and bisulfite). The thiazine dyestuff acts as a redox sensitive material, having different visual properties in the oxidised and reduced forms. Other suitable redox sensitive materials include an oxazine dyestuff, an azine dyestuff, a triphenylmethane dyestuff, an indophenol dyestuff, and indigo dyestuff, proflavin, viologen and/or mixtures thereof.

In place of a redox sensitive material, the following materials may be used: a carbon monoxide sensitive material, a carbon dioxide sensitive material, an oxygen sensitive material, an amine sensitive material and an ammonia sensitive material.

Various carbon dioxide sensitive materials can be used, such as: m-Cresol Purple (MCP, Hydroxy triarylmethane), Thymolphthalein (3,3-bis(4-hydroxy-2-methyl-5-propan-2-ylphenyl)-2-benzofuran-1-one), o-Cresolphthalein, Acryloly florescein (AcF1), 13-methyl umbelliferon (BMUB), Bromothymol blue (BTB, Hydroxy triarylmethane), 5' and 6-Carboxyseminaphtholfluorescein (c-SNAFL), S' and 6'-Carboxyseminaphtholrhodamine (c-SNARF), Cresol Red (CR, o-Cresolsulfonephthalein), Hexadecyl trimethyl ammonium cation (CTA), Hexadecyl trimethyl ammonium hydroxide (CTAH), Dual lumophore referencing (DLR), 2-(2,4-Dinitrophenylaxo)-1-naphthol-3,6-disulphonic acid (DNPA), tris(thenoyltrifluoroacetonato) europium (III) (Eu(tta)1), Fluorescein (FI, resorcinolphthalein), 7-hydroxycoumarin-4-acetic acid (HCA), 1, Hydroxypyrene-3,6,S-trisulphonic acid (HPTS), Neutral red (NR, toluylene red), Phenol Red (PR, phenolsulfonphthalein), Rhodamine 6G (R6G), Sulforhodamine 101 (SRh), Thymol blue (TB, thymolsulphonephthalein) and Texas Red hydrazine (THR).

Various amine or ammonia sensitive materials can be used, such as: Bromophenol Blue (BPB, Hydroxy triarylmethane), Bromocresol Green (BCG, Hydroxy triarylmethane), Bromocresol Purple (BCP, Hydroxy triarylmethane), Bromothymol Blue (BTB, Hydroxy triarylmethane), Phloxine Blue (PB, Fluorone), Thymol Blue (TB, Hydroxy triarylmethane), and m-Cresol Purple (MCP, Hydroxy triarylmethane).

The glycerol acts as an electron donor. Other suitable electron donors include mild reducing agents such as an amine, a reducing saccharide, a readily oxidisable polymer, glycerol, trihydroxyhexane or other general anti-oxidants. These only act in the presence of the semiconductor material, and cannot reduce the redox sensitive material in its absence.

The $TiO_2$ acts as a semiconductor material specifically sensitive to light having a wavelength of about 200-400 nm. Irradiation of the semiconductor material by light having a wavelength of about 200-400 nm causes an electron to be donated by the electron donor to the semiconductor material which in turn provides an electron to the redox sensitive material causing the redox sensitive material to become reduced. Alternative semiconductor materials include oxides of: titanium, tin, tungsten, zirconium, and zinc and mixtures thereof. In particular the semiconductor material may be selected from one or more the group consisting of: titanium (IV) oxide ($TiO_2$), strontium titanate ($SrTiO_3$), tin (IV) oxide ($SnO_2$), tungsten (IV) oxide ($WO_3$), zirconium (IV) oxide ($ZrO_2$), zinc (II) oxide (ZnO) and mixtures thereof.

The sodium dithionite acts as a reducing agent and is incorporated into the non-UV activatable ink. Alternative reducing agents include other dithionites, sulphites, and ascorbic acid. The reducing agent may include further components. For example, when the reducing agent is ascorbic acid, it may also comprise hydrochloric acid.

In the examples given the release layer is glassine. It will be appreciated that alternative release layers such as siliconised glassine paper, and a silicon treated polymer may also be used.

The adhesive layers described in both the indicator and the barrier layers may be a rubber based hot melt, an acrylic adhesive, a varnish coated adhesive, an adhesive kill treated adhesive, a treated or coated permanent acrylic, a patterned adhesive or a treated (or coated) peelable acrylic.

Various modifications and variations to the described embodiments of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes of carrying out the invention which are obvious to those skilled in the art are intended to be covered by the present invention.

What is claimed is:

1. An indicator device for indicating the passage of time, the indicator device comprising:
    an indicator section, a barrier section adjacent to the indicator section, and a first adhesive layer;
    the barrier section comprising:
      a removable barrier layer; and
    the indicator section comprising:
      an indicator material;
      a substrate material; and
      a chemical agent;
    wherein the indicator material and the substrate material are incorporated into a combined indicator and substrate layer, and wherein the combined indicator and substrate layer comprises the chemical agent; and
    wherein the first adhesive layer is at least one of: (i) located between the barrier section and the combined indicator and substrate layer; and (ii) located adjacent to the combined indicator and substrate layer and adjacent to the barrier section;
    the indicator material displaying different visible properties in response to the presence or absence of the chemical agent;
    wherein the removable barrier layer is substantially impermeable to the chemical agent;
    wherein upon removal of the removable barrier layer, the concentration of the chemical agent in the indicator section decreases over time, effecting a change in visible properties of the indicator material.

2. The indicator device of claim 1, wherein the chemical agent diffuses out of the indicator section.

3. The indicator device of claim 1, wherein the indicator device further comprises a second adhesive layer, wherein the combined indicator and substrate layer is located between the first adhesive layer and the second adhesive layer.

4. The indicator device of claim 1, wherein the combined indicator and substrate layer further comprises a reference section, optionally comprising a reference ink.

5. The indicator device of claim 4, wherein the combined indicator and substrate layer is divided into two or more portions, a first portion comprising the reference section and a second portion comprising the indicator material.

6. The indicator device of claim 5, wherein the barrier section is sized to cover only one of the first and second portions.

7. The indicator device of claim 1, wherein the first adhesive layer is larger in width than the combined indicator and substrate layer in at least one axis such that the adhesive layer caps the combined indicator and substrate layer by covering a first side of the combined indicator and substrate layer and by covering one or more edges of the combined indicator and substrate layer.

8. The indicator device of claim 7, wherein the barrier section is larger in width than the combined indicator and substrate layer in at least one axis.

9. The indicator device of claim 1, wherein the combined indicator and substrate layer comprises a polymer binder optionally selected from one or more of the group consisting of: polyvinyl butyral (PVB), nitrocellulose (NC), polyvinyl alcohol (PVA), hydroxyethyl cellulose (HEC), and hydroxypropyl cellulose (HPC).

10. The indicator device of claim 1, wherein the combined indicator and substrate layer comprises a plasticiser optionally selected from one or more of the group consisting of: tributyl phosphate, diisodecyl adipate, tris-2-ethylhexyl phosphate, glycerol, and dimethyl phthalate.

11. The indicator device of claim 1, wherein the indicator material and the substrate material are incorporated into the same layer so forming the combined indicator and substrate layer, and wherein at least one of: (a) the indicator material is dispersed within the substrate material or, (b) the substrate material is dispersed within the indicator material.

12. The indicator device of claim 1, wherein the combined indicator and substrate layer further comprises a reference section, optionally comprising a reference ink.

13. The indicator device of claim 12, wherein the combined indicator and substrate layer is divided into two or more portions, a first portion comprising the reference section and a second portion comprising the indicator material.

14. The indicator device of claim 13, wherein the barrier section is sized to cover only one of the first portion and the second portion.

15. The indicator device of claim 12, wherein the combined indicator and substrate layer is divided into at least a first portion and a second portion, wherein one of: (a) the first portion comprises the indicator material after exposure to the chemical agent, and the second portion comprises the indicator material before exposure to the chemical agent; or (b) the first portion comprises the indicator material before exposure to the chemical agent, and the second portion comprises the indicator material after exposure to the chemical agent; wherein the first portion is the reference section, or the second portion is the reference section.

16. The indicator device of claim 1, wherein the indicator material is selected from one or more of the group consisting of: a redox sensitive material, a carbon monoxide sensitive material, a carbon dioxide sensitive material, an oxygen sensitive material, an amine sensitive material, and an ammonia sensitive material.

17. The indicator device of claim 1, further comprising a release section adjacent to the indicator section and detachable from the indicator section.

18. The indicator device of claim 17, wherein the indicator section is located between the release section and the barrier section.

19. The indicator device of claim 1, wherein the barrier section comprises a reference ink.

20. The indicator device of claim 1, wherein the barrier section comprises a detachable section and a fixed section, wherein the removable barrier layer of the barrier section is the detachable section.

21. The indicator device of claim 1, wherein the chemical agent is at least one of an oxidizing agent, water, carbon dioxide, amines, acids, carboxylic acids, ammonium hydroxide, and ammonia.

* * * * *